United States Patent

Aristoff et al.

[11] Patent Number: 4,975,537
[45] Date of Patent: Dec. 4, 1990

[54] $\Delta^{9(11)}$-ANGIOSTATIC STEROIDS

[75] Inventors: Paul A. Aristoff, Portage; Harvey I. Skulnick; Wendell Wierenga, both of Kalamazoo, all of Mich.

[73] Assignee: The Upjohn Company, Kalamazoo, Mich.

[21] Appl. No.: 351,977

[22] Filed: May 15, 1989

Related U.S. Application Data

[63] Continuation-in-part of Ser. No. 87,228, Jun. 19, 1987, abandoned, which is a continuation-in-part of Ser. No. 790,564, Oct. 23, 1985, abandoned, which is a continuation-in-part of Ser. No. 811,866, Dec. 20, 1985, abandoned.

[51] Int. Cl.$^5$ .......................... C07J 21/00; C07J 43/00
[52] U.S. Cl. ............................................. 540/9; 540/95; 540/96; 552/501; 552/585; 552/592
[58] Field of Search ................................ 540/9, 95, 96; 260/397.45; 552/507, 585, 592

[56] References Cited

U.S. PATENT DOCUMENTS 2,640,839 6/1953 Wendler et al. ............... 260/397.45
3,045,033 7/1982 Gould et al. ................... 260/397.45

Primary Examiner—Mukund J. Shah
Assistant Examiner—Edward C. Ward

[57] ABSTRACT

Disclosed are $\Delta^{9(11)}$-steroids of the formula

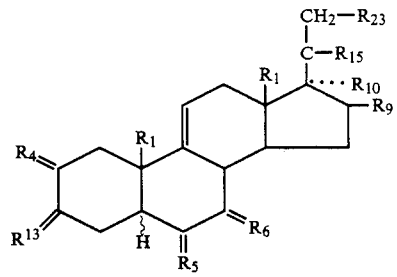

which have been found to be angiostatic and therefore are useful in the control of embryogenesis, inflammatory conditions, tumor growth as well as other abnormalities.

7 Claims, No Drawings

$\Delta^{9(11)}$-ANGIOSTATIC STEROIDS

The present patent application is a continuation of U.S. patent application Ser. No. 07/087,228 filed June 19, 1987 now abandoned, which is a national application of PCT application No. 86/02189 filed Oct. 16, 1986, which is a continuation-in-part of co-pending application Ser. Nos. 06/790,564 filed Oct. 23, 1985, now abandoned, and No. 06/811,866 filed Dec. 20, 1985 now abandoned.

BACKGROUND OF THE INVENTION

Angiogenesis is the development of blood vessels which typically would lead to a vascular bed capable of sustaining viable tissue. Angiogenesis is a necessary process in the establishment of embryonic tissue and development of a viable embryo. Similarly angiogenesis is a necessary step in the establishment and development of tumor tissue as well as certain inflammatory conditions. The inhibition of angiogenesis obviously could be useful in the control of embryogenesis, inflammatory conditions, and tumor growth, as well as numerous other conditions as set forth in more detail hereinafter.

Co-pending application Ser. No. 701,601 filed Feb. 14, 1985 describes a novel class of solution stable non-glucocorticoid steroids which are useful in the inhibition of angiogenesis.

Co-pending application Ser. No. 781,100 filed Sept. 27, 1985 and Ser. No. 790,564 filed Oct. 23, 1985 describe the use of non-glucocorticoid steroids in the inhibition of angiogenesis. Also co-pending application Ser. No. 775,204 filed Sept. 12, 1985 describes a novel class of 20- and 21-aminosteroids which are useful as antiangiogenic agents.

European application No. 83870132.4 (Publication No. 0 114 589) published Aug. 1 1984, describes the use of cortisone, hydrocortisone and 11α-hydrocortisone in combination with heparin in the inhibition of angiogenesis.

J. Folkman, et al., Science 221, 719–725 (1983), further describes the angiogenesis inhibitory effects of heparin and heparin fragments in combination with cortisone. Folkman further elaborates on the use of heparin or heparin fragments in combination with hydrocortisone in the Proceedings of AACR 26, 384–385 (March 1985). Also see R. Crum, et al., Science 230, 1375–1378 (1985).

FIELD OF INVENTION

The present invention is novel 4,5-dihydro and tetrahydro steroids and formulations thereof which have pharmacologically useful properties.

SUMMARY OF INVENTION

The compounds of the present invention are novel steroids and are represented generically by general Formula I (see Formula Chart) wherein the various substituents have the following meanings: wherein $R_1$ is $\beta$-CH$_3$ or $\beta$-CH$_2$H$_5$; wherein $R_2$ is H, and $R_3$ is =O, —OH, —O—alkyl(C$_1$C$_{12}$), —OC(=O)alkyl(C$_1$–C$_{12}$), —OC(=O)aryl, —OC(=O)N(R)$_2$, or $\alpha$-OC(=O)OR$_7$, wherein aryl is furyl, thienyl, pyrrolyl, or pyridyl wherein each of said hetero moiety is optionally substituted with one or two (C$_1$–C$_4$)alkyl groups or aryl is —(CH$_2$)$_f$-phenyl wherein f is 0 to 2 and wherein the phenyl ring is optionally substituted with 1 to 3 groups selected from chlorine, fluorine, bromine, alkyl(C$_1$–C$_3$), alkoxy(C$_1$–C$_3$), thioalkoxy(C$_1$–C$_3$), Cl$_3$C—, F$_3$C—, —NH$_2$ and —NHCOCH$_3$ and wherein R is hydrogen, alkyl(C$_1$–C$_4$), or phenyl and each R can be the same or different; and wherein $R_7$ is aryl as herein defined or alkyl(C$_1$–C$_{12}$); or wherein $R_2$ is $\alpha$-Cl and $R_3$ is $\beta$-Cl; or wherein $R_2$ and $R_3$ taken together are oxygen (—O—) bridging positions C-9 and C-11; or wherein $R_2$ and $R_3$ taken together form a double bond between positions C-9 and C-11; or $R_2$ is $\alpha$-F and $R_3$ is $\beta$-OH; wherein $R_4$ is H, CH$_3$, Cl or F; wherein $R_5$ is H, OH, F, Cl, Br, CH$_3$, phenyl, vinyl or allyl; wherein $R_6$ is H or CH$_3$; wherein $R_9$ is H, OH, CH$_3$, F or =CH$_2$; wherein $R_{10}$ is H, OH, CH$_3$ or $R_{10}$ forms a second bond between positions C-16 and C-17; wherein $R_{12}$ is —H or forms a double bond with $R_{14}$; wherein $R_{13}$ is H, —OH, —OH, =O, —O—P(O)(OH)$_2$, or —O—C(=O)—(CH$_2$)$_t$COOH where t is an integer from 2 to 6; wherein $R_{14}$ is H or forms a double bond with $R_{12}$; wherein $R_{15}$ is =O or —OH; wherein $R_{23}$ with $R_{10}$ forms a cyclic phosphate as depicted by Formula II; wherein $R_9$ and $R_{15}$ have the meaning defined above; or wherein $R_{23}$ is —OH, O—C(=O)—R$_{11}$, —O—P(O)(OH)$_2$, or —O—C(=O)—(CH$_2$)$_t$COOH wherein t is an integer from 2 to 6; and $R_{11}$ is —Y—(CH$_2$)$_n$—X—(CH$_2$)$_m$—SO$_3$H, —Y'—(CH$_2$)$_p$—X'—(CH$_2$)$_q$—NR$_{16}$R$_{17}$ or —Z(CH$_2$)$_r$Q, wherein Y is a bond or —O—; Y' is a bond —O—, or —S—; each of X and X' is a bond, —CON(R$_{18}$)—, —N(R$_{18}$)CO—, —O—, —S—, —S(O)—, or —S(O$_2$)—; R$_{18}$ is hydrogen or alkyl(C$_1$–C$_4$); each of R$_{16}$ and R$_{17}$ is a lower alkyl group of from 1 to 4 carbon atoms optionally substituted with one hydroxyl or R$_{16}$ and R$_{17}$ taken together with the nitrogen atom to which each is attached forms a monocyclic heterocyclic selected from pyrrolidino, piperidino, morpholino, thiomorpholino, piperazino or N(lower)alkylpiperazino wherein alkyl has from 1 to 4 carbon atoms; n is an integer of from 4 to 9; m is an integer of from 1 to 5; p is an integer of from 2 to 9; q is an integer of from 1 to 5; Z is a bond or —O—; r is an integer of from 2 to 9; and Q is (1) —R$_{19}$—CH$_2$COOH wherein R$_{19}$ is —S—, —S(O)—, —S(O)$_2$—, —SO$_2$N(R$_{20}$)—, or —N(R$_{20}$)SO$_2$—; and R$_{20}$ is hydrogen or lower alkyl(C$_1$–C$_4$); with the proviso that the total number of carbon atoms in R$_{20}$ and (CH$_2$) , is not greater than 10;

(2) —CO—COOH, or (3) —CON(R$_{21}$)CH(R$_{22}$)COOH wherein R$_{21}$ is H and R$_{22}$ is H, CH$_3$, —CH$_2$COOH, —CH$_2$CH$_2$COOH, —CH$_2$OH, —CH$_2$SH$_3$, or —CH$_2$CH$_2$SCH$_3$, or —CH$_2$-Ph—OH wherein Ph—OH is p-hydroxyphenyl; or R$_{21}$ is CH$_3$ and R$_{22}$ is H; or R$_{21}$ and R$_{22}$ taken together are —CH$_2$CH$_2$CH$_2$—; or —N(R$_{21}$)CH(R$_{22}$)COOH taken together is —NHCH$_2$CONHCH$_2$COOH; and pharmaceutically acceptable salts thereof; with the proviso that except for the compound wherein each of $R_1$ is $\beta$-CH$_3$, $R_2$ and $R_3$ taken together form a double bond between positions 9 and 11, each of $R_4$ and $R_3$ is hydrogen, $R_{12}$ and $R_{14}$ taken together form a double bond between positions 4 and 5, $R_3$ is $\alpha$-F, $R_9$ is $\beta$-CH$_3$, $R_{10}$ is $\alpha$-OH, each of $R_{13}$ and $R_{15}$ is =O and $R_{23}$ is —OP(O)—(OH)$_2$, $R_{13}$ =O only when $R_{13}$ with $R_{10}$ forms the above described cyclic phosphate. Excepted from the compounds of Formula I is the compound 3$\alpha$,11$\beta$,17$\alpha$,21-tetrahydroxy-5$\beta$-pregnane-20-one.

Unless specified otherwise all substituent groups attached to the cyclopenta phenanthrene moiety of Formula I may be in either the alpha or beta position.

Pharmaceutically useful formulations of the compounds of Formula I are also a part of the present invention.

The use of the compounds of Formula I as anti-angiogenesis agents is also a part of the present invention. Further the use of the compounds of Formula I in combination with heparin or heparin fragments as anti-angiogenic combination therapy is a part of the present invention.

Preferred embodiments of this invention are compounds of Formula I wherein $R_{13}$ is OH and each of $R_{12}$ and $R_{14}$, is hydrogen and the use of these compounds in combination with heparin or a heparin fragment as anti-angiogenesis agents. Other preferred embodiments of the present invention are compounds wherein $R_5$ is $CH_3$, F, Cl, Br, H or OH, and more preferably $R_3$ is in the α-position and is $CH_3$, H or F; or wherein $R_{10}$ is α-H or α-OH; or wherein $R_2$ is hydrogen and $R_3$ is in the α-position and is OH, —O—alkyl(-$C_1$-$C_6$), —OC(=O)alkyl($C_1$-$C_6$), —OC(=O)aryl, —O—C(=O)N(R)$_2$ or —O—C(=O)$R_7$; or wherein $R_{15}$ is =O, Additionally compounds wherein $R_2$ and $R_3$ together form a double bond or together represent an oxa group between C-9 and C-11 are preferred. Particularly preferred is the compound 21-phosphate-6α-fluoro-17-hydroxy-16β-methyl(pregna-4,9(11)-diene)-3,20-dione and mono and bis salts thereof, in particular the disodium salt thereof. The use of all the preferred compounds as anti-angiogenic agents alone or preferably in combination with heparin or a heparin fragment is also a preferred embodiment of the present invention.

Pharmacologically acceptable salts of the compounds of Formula I include acid addition salts and quaternary ammonium salts when $R_{11}$ is Y'—(CH$_2$)$_p$—X'—(CH$_2$-)$_q$—NR$_{16}$R$_{17}$. Illustrative examples of such acid addition salts are inorganic salts such as hydrochloride, hydrobromide, sulfate, or phosphate, or organic salts such as acetate, malonate, succinate or sulfonates. Quaternary ammonium salts of compounds of Formula I containing a terminal amine group may be depicted as follows wherein $R_{11}$ is —Y'—(CH$_2$)$_p$—X'—(CH$_2$)$_q$—N-(alkyl)—(R$_{16}$)(R$_{17}$) $R_8^{(-)}$ wherein Y', p, X', q, $R_{12}$ and $R_{13}$ have the meanings defined in Formula I, alkyl has from one to 4 carbon atoms, and $R_8^{(-)}$ represents an anion, for example $R_8$ is I, Br, Cl, $CH_3SO_3$ or $CH_3COO$.

To form acid addition salts of the compounds of Formula I containing a terminal amine function, said compounds are treated with suitable pharmaceutically acceptable inorganic or organic acids by standard procedures. Suitable inorganic acids are, for example, hydrochloric, hydrobromic, nitric, sulfuric or phosphoric acids. Suitable organic acids include carboxylic acids, such as, acetic, propionic, glycolic, lactic, pyruvic, malonic, succinic, fumaric, malic, tartaric, citric, stearic, ascorbic, maleic, hydroxymaleic, benzoic, hydroxybenzoic, phenylacetic, glutamic, glutaric, cinnaminc, salicylic, 2-phenoxybenzoic or sulfonic acids such as methane sulfonic, sulfonilic, toluenesulfonic, or 2-hydroxyethanesulfonic. The quaternary ammonium salts are formed by contacting said compounds with a suitable akylating agent such as dimethyl sulfate, diethyl sulfate, or a suitable alkyl halide such as methyl or ethyl chloride or methyl or ethyl bromide or methyl or ethyl iodide.

Also included within the scope of this invention are base addition salts of compounds of Formula I wherein $R_{23}$ is —O—P(O)(OH)$_2$ or —O—C(=O)—(CH$_2$)$_t$-COOH or wherein $R_{11}$ is —Y—(CH$_2$)$_n$—X—(CH$_2$)$_m$SO$_3$H or —Z(CH$_2$)$_r$Q or wherein $R_{23}$ and $R_{10}$ form a cyclic phosphate which are obtained by treating the acid of Formula I with pharmaceutically acceptable inorganic or organic bases by standard procedures. Suitable inorganic bases are, e.g., those of alkali metal hydroxides, such as potassium, sodium, magnesium, and aluminum. Suitable organic bases are physiologically acceptable amines such as choline(OH$^-$), tris(hydroxymethyl)methylamine, triethanolamine, ethanolamine, tripropylethylene diamine, ethylene diamine, piperazine, diethylamine, lysine, morpholine, and ammonia or trialkylamines such as triethylamine. Mono and bis salts are within the scope of this invention. When $R_{23}$ is —O—P(O)(OH)$_2$ or when $R_{23}$ and $R_{10}$ together form a cyclic phosphate mono or bis acid addition salts of these compounds can be formed and are within the scope of pharmaceutically acceptable salts of the present invention.

Particularly preferred salts of the compound 21-phosphate-6α-fluoro-17-hydroxy-16β-methyl(pregna-4,9(11)-diene)-3,20-dione are the mono and bis salts formed with sodium, calcium, magnesium, potassium and lithium and amine salts such as tris-hydroxy-6-butylamine, ethanolamine, triethanolamine, tripropylethylene diamine, ethylene diamine, piperazine, diethylamine, lysine, morpholine and ammonia.

The aryl moiety in the $R_3$ group —OCOaryl is attached to the carbonyloxy moiety through any of the available ring carbon atoms of said aryl moiety.

Any reference herein to compounds of Formula I includes pharmacologically acceptable salts thereof.

The compounds of the present invention are useful in treating the following diseases and injuries: head trauma, spinal trauma, septic or traumatic shock, stroke, and hemorrhagic shock. In addition, utility in cancer as well as other disorders or physiological phenomena dependent on angiogenesis such as embryo implantation (antifertility), arthritis, and atherosclerosis is exhibited with these compounds optionally co-administered with oral heparin or systemic heparin fragments (see J. Folkman, et al., Science 32, 719-725 (1983). The compounds of the present invention possess substantially none of the typical glucocorticoid effects.

The steroids of Formula I can be administered orally, intramuscularly, intravenously and by suppository, and the effective dosage range is 10 to 1500 mg/kg/day. The compounds of the present invention may be coadministered with low doses of glucocorticoids. For the treatment of cancer including head tumors and other conditions dependent upon angiogenesis a preferred dosage range of a compound of Formula I is 50 to 500 mg/kg/day for 30 days repeated for 30 additional days after a 30 day respite or on a chronic intermittent basis such as every other day therapy until tumor regression or absence of metastases is observed. The preferred route of administration is orally, by suppository or intramuscularly. For the treatment of arthritis the preferred dosage range of a compound of Formula I is 10 to 250 mg/kg/day or every other day until absence or significant reduction in associated symptoms is observed. For the treatment of atherosclerosis the preferred dosage range of a compound of Formula I is 10 to 250 mg/kg/day or every other day chronically. And, for the disruption of or prevention of embryo implantation the preferred dosage range of a compound of Formula I is 10 to 250 mg/kg/day chronically to fertile women. When coadministering a compound of Formula I with heparin or a heparin fragment in practicing the present invention the amount of heparin or heparin to be utilized varies from 1,000 to 50,000 units/kg/day with heparin being administered orally and heparin fragments being administered subcutaneously, orally, intramuscularly or intravenously.

With respect to the compound 21-phosphate-6α-fluoro-17-hydroxy-16β-methyl(pregna-4,9(11)-diene)-3,20-dione and salts thereof, the preferred dosage regimen is as follows: The compound and salts thereof can be administered orally, intramuscularly, intravenously and by suppository, and the effective dosage range is 10 to 1500 mg/kg/day. Additionally, a dosage regimen of using a loading dose of about 30 mg/kg followed by a repetitive as needed maintenance dose of about 15 mg/kg may be desirable. The compound and its salts may be coadministered with low doses of glucocorticoids. For the treatment of cancer including head tumors and other conditions dependent upon angiogenesis a preferred dosage range is 50 to 1500 mg/kg/day for 30 days repeated for 30 additional days after a 30 day respite or on a chronic intermittent basis such as every other day therapy until tumor regression or absence of metastases is observed The preferred route of administration is orally, by suppository or intramuscularly. For the treatment of arthritis the preferred dosage range is 10 to 250 mg/kg/day or every other day until absence or significant reduction in associated symptoms is observed. For the treatment of atherosclerosis the preferred dosage range is 10 to 250 mg/kg/day or every other day chronically. And, for the disruption of or prevention of embryo implantation the preferred dosage range is 10 to 250 mg/kg/day chronically to fertile women. When coadministering the compound and its salts with heparin or a heparin fragment in practicing the present invention the amount of heparin or heparin to be utilized varies from 1,000 to 50,000 Units/kg/day with heparin being administered orally and heparin fragments being administered subcutaneously, intramuscularly or intravenously.

The utility of the compounds of the present invention can be demonstrated in various test models as follows: For head trauma, mice are struck on the head with a standard weight which is dropped from a set height. They are then dosed subcutaneously with the test compound. After one hour the motor abilities of the mice are assessed. Active test compounds promote improved motor activity relative to controls. For spinal trauma, see E. D. Hall and J. M. Braughler Surg. Neurol. 18, 320–327 (1982) and J. Neurosurg. 56, 838–844 (1982). Septic (traumatic) shock is demonstrated in a rat model whereby test compound is administered and protection of the rats from the lethal effects of endotoxin is measured. For stroke, the carotid arteries of gerbils are ligated for a brief period after which test compound is administered subcutaneously. The behavior of the gerbils is observed after a recovery period, and gerbils receiving test compound display a more normal behavior after the recovery period. And for hemorrhagic shock, by published procedures used to evaluate glucocorticoids. The inhibition of angiogenesis associated with tumor formation and proliferation is typically evaluated in the chick embryo or rabbit cornea, e.g., as reported by J. Folkman, et al. Science 221, 719–725 (1983). Illustratively 21-phosphate-6α-fluoro-17-hydroxy-16β-methyl(pregna-4,9(11)-diene)-3,20-dione and the disodium salt thereof when administered at a dosage of 50 μg per 10 μl of polymeric vehicle in 12–16 chick embryos in the presence of 50 μg per 10 μl of HEPAR (trademark of HEPAR International, P.O. Box 338, 150 Industrial Drive, Franklin, Ohio 45005) heparin inhibited angiogenesis by 58% and 40% respectively of control. Administration of 5 mg of the disodium salt twice daily orally in combination with daily HEPAR heparin (orally) to mice bearing SC M5076 reticulum cell sarcoma (300 mm$^3$ implant) resulted in inhibition of tumor growth and in some cases tumor regression.

Sterile aqueous solutions of the compounds of Formula I typically will contain other components such as preservatives, anti. oxidants, chelating agents, or other stabilizers. Suitable preservatives can include benzyl alcohol, the parabens, benzalkonium chloride, or benzoic acid. Anti-oxidants such as sodium bisulfite, ascorbic acid, propyl 3,4,5-trihydroxy benzoate, and the like may be employed. Chelating agents such as citrate, tartrate, or ethylenediaminetetraacetic acid (EDTA) may be used. Other additives useful as stabilizers of corticosteroid prodrugs (e.g., creatinine, polysorbate 80, and the like) may be employed.

Sterile aqueous solutions of compounds of Formula I can be administered to the patient being treated, i.e., a warm blooded mammal, including humans, intramuscularly or intravenously or orally. Additionally conventional solid dosage forms of the compounds of Formula I can be administered orally to the patient being treated. For example, capsules, pills, tablets or powders of the compounds of Formula I can be formulated in unit dosage forms incorporating conventional fillers, dispersants, preservatives and lubricants. Also suppositories providing a sustained release of a compound of Formula I can be formulated using conventional inert materials such as biodegradable polymers or synthetic silicones.

Heparin fragment means any part of the heparin compound having substantially the same type of anti-angiogenic activity as heparin.

The compounds of the present invention wherein $R_{23}$ is —O—C(=O)—$R_{11}$ provide certain advantages over known steroids in that these novel compounds are highly water soluble which facilitates formulation of the compounds and permits long term storage of solutions of said novel compounds.

The solution stability of these compounds is due to several features: (1) The derivatives are highly soluble in the pH range 3 to 6 which is the pH range in which ester hydrolysis in aqueous solution is minimized. (2) Functional groups which may promote ester hydrolysis through any catalytic or substituent effect are sufficiently distant from the ester linkage that such influences are minimized. (3) The compounds self-associate in concentrated solutions to form molecular aggregates which increase the shelf life of formulations by (a) retarding hydroxide ion catalyzed ester hydrolysis at high concentrations, and (b) solubilizing any parent steroid present in and resulting from the hydrolysis of a solution of a compound of the present invention. For storage of aqueous solutions of the compounds of Formula I wherein $R_{23}$ is —O—(—O)$R_3$ the pH of their solution must be properly controlled to accomplish the storage advantages. Ideally, the pH will be maintained at a level where the hydrolysis of the ester is at a minimum. This minimum depends to a certain degree on the chemical structure of the pro-moiety, the formulation concentration, and the temperature of storage but in general will be at a pH of about 3 to 6 for the compounds of this invention. A pH of 4 to 5 is preferred for compounds wherein $R_{11}$ is —CH$_2$CH$_2$COOH. Most advantageously, buffers should be employed to maintain the pH at or near the desired level throughout the shelf life of the formulation. Suitable buffers are those which are physiologically acceptable and exhibit sufficient buffer capacity in the pH range 3–6, e.g., acetate, citrate, succinate, or phthalate buffers and the like. The quantity of buffer used is determined by means known in the art and will depend on the pH desired, the concentration of the solution, and the buffering capacity of the buffer.

The compounds of the present invention are prepared by various means all of which are well known in the art. Compounds wherein $R_{is\ OH}$, $R_{13}$ is =O, and $R_{12}$ and $R_{14}$ taken together form a double bond between C-4 and C-5 are generally known in the art. Reduction of such known compound to obtain compounds wherein R s is =O, $R_{23}$ is OH and each of $R_{23}$ and $R_{14}$ is hydrogen is achieved by generally known hydrogenation procedures. e.g., catalytic hydrogenation using palladium on charcoal in ethyl acetate at elevated temperatures. A variety of well known solvents could be used. Generally the hydroxyl group represented by $R_{23}$, i e., the hydroxyl group at C-21 would be protected as an acetate, a silky group, or preferably a benzoate prior to the reduction of the 4,5-double bond. The compound thus obtained, a compound wherein $R_{13}$ is =O, each of $R_{12}$ and $R_{14}$ is hydrogen and $R_{23}$ is either OH or a protected OH group can be used to prepare the compound of Formula I wherein $R_{13}$ is =O and $R_{23}$ taken together with $R_{10}$ forms a cyclic phosphate moiety by first deprotecting the C-21 hydroxyl using base hydrolysis then converting the C-21 hydroxyl to a phosphate by procedures generally described in U.S. Pat. No. 3,966,778. The phosphate is then converted to the cyclic phosphate by procedures generally described in J. Med. Chem. 28, 418–422 (1985). Alternatively, the procedure of U.S. Pat. No. 3,045,033 may be employed.

Of course the conversions at C-21 to form the cyclic phosphate compound wherein $R_{13}$ is =O could have been carried out prior to reduction of the 4,5-double bond to give compounds of Formula I wherein $R_{13}$ is =O, $R_{12}$ and $R_{14}$ form a double bond between C-4 and C-5 and $R_{13}$ together with $R_{10}$ forms the cyclic phosphate group.

The compounds obtained above wherein $R_{13}$ is =O, each of $R_{12}$ and $R_{14}$ is hydrogen and $R_{23}$ is OH or a protected hydroxyl group can be further used to make the corresponding compounds wherein $R_{13}$ is hydroxyl, $R_{12}$ and $R_{14}$ are hydrogen and $R_{23}$ is OH or a protected OH group by further reduction of said compound using hydride reducing agents such as sodium borohydride when $R_{23}$ is hydroxy and Rancy nickel regioselective reduction (H. Hosoda, et al., Chem. Pharm. Bull. 31, 4001–4007 (1983) when $R_{23}$ is protected as, e.g., an acetate or benzoate. The initial reduction of the 4,5-double bond will give a mixture of compounds wherein the hydrogen at C-5 is $\alpha$ and $\beta$ and said compounds can be separated chromatographically. Similarly the reduction of the C-3 ketone will give a mixture of compounds wherein the hydroxyl is $\alpha$ and $\beta$ and these isomers similarly can be separated using chromatographic techniques. The resulting compounds, following, the second above described reduction at C-3, are those wherein $R_{13}$ is OH, $R_{12}$ and $R_{14}$ are hydrogen, $R_{23}$ is OH or a protected OH in which latter case the protecting group can be removed by base hydrolysis and the compounds used to prepare others of Formula I. To prepare compounds of Formula I wherein $R_{23}$ and/or $R_{13}$ is a phosphate group the general procedure of U.S. Pat. No. 3,966,778 referenced above is employed. Of course the $R_{23}$ primary alcohol will preferentially react, thus to prepare compounds wherein $R_{13}$ is a phosphate and $R_{23}$ is OH, it will be necessary to selectively protect the $R_{23}$ OH prior to converting the $R_{13}$ OH to a phosphate. Such selective protection can be achieved using, e.g., diphenylmethyl silyl or diphenylbutyl silyl protecting groups which can be subsequently removed with fluoride, e.g., tetrabutylammonium fluoride. Alternatively, the $R_{13}$ phosphate group can be introduced prior to the aforementioned base hydrolysis of the $R_{23}$ benzoate group.

The compounds of Formula I wherein $R_{13}$ is hydrogen are prepared by treating a corresponding compound wherein $R_{23}$ is a protected hydroxyl, preferably a benzoate, and $R_{13}$ is OH with a leaving group such as tosyl chloride or mesyl chloride to give the tosylate or mesylate at C-3, displacing the leaving group with iodide by treatment with sodium iodide then subjecting the compound to reductive dehalogenation using catalytic reduction or hydride reduction means.

The $R_{15}$ keto group can be reduced to the $R_{15}$ hydroxyl group by using hydride reducing reagents, e.g., sodium borohydride in isopropyl alcohol. This reduction can be carried out either prior to or subsequent to the reduction of the 4,5-double bond.

The compounds of Formula I wherein $R_{23}$ is —O—C(=O)—$R_{11}$ or —O—C(=O)—(CH$_2$)$_t$COOH are prepared as follows. These changes at the C-21 position of the compounds of Formula I would generally be carried out subsequent to the hydrogenation steps described above. In the following description for convenience the symbol St is employed to represent that portion of Formula I as depicted by Formula III wherein the various symbols set forth therein have the meanings defined in Formula I.

PREPARATION OF COMPOUNDS OF FORMULA I WHEREIN $R_{11}$ IS —Y—(CH$_2$)$_n$—X—(CH$_2$)$_m$SO$_3$H

When Y is oxy, i.e., —O—, equimolar amounts of an intermediate of the formula O$_2$N(C$_6$H$_4$)—OCOO—(CH$_2$)$_n$—X—(CH$_2$)$_m$SO$_3$H (Formula IV) wherein (C$_6$H$_4$) is 1,4-phenylene and n, m, and X have the meanings defined in Formula I, and a parent steroid of the formula StOH wherein St has the meaning defined in Formula III are reacted in a dry aprotic solvent such as tetrahydrofuran (THF), dimethylformamide (DMF) or dimethylsulfoxide (DMSO), in the presence of an acylation catalyst such as dimethylaminopyridine (DMAP) or N-methylimidazole. Although the reaction may be performed at room temperature it is convenient to gently warm the reaction mixture to about 50°–60° C. with stirring until all the activated carbonate ester is consumed. The product is purified by pouring the reaction mixture into water with the pH adjusted to ~4 and washing with an organic solvent, e.g., ether or ethyl acetate. It is then concentrated by removing the solvent and further purified either as the free acid or as an appropriate salt by crystallization and/or chromatography.

When Y is a bond equimolar amounts of an intermediate of the formula HOOC(CH$_2$)$_n$—X—(CH$_2$)$_m$—SO$_3$H (Formula V) wherein n, m, and X have the meanings defined in Formula I with a 21-iodo or 21-O-mesyl derivative of the parent steroid which may be represented respectively b the formulas St-Iodo (Formula VI) and St-O-mesyl (Formula VII) wherein St has the meaning defined in Formula III and mesyl means —S(O$_2$)—CH$_3$ are reacted. When the 21-iodo steroid derivative is employed the reaction proceeds at room temperature, whereas when the 21-O-mesyl steroid derivative is used the reaction is heated to about 60°–70°C. The reaction is carried out in a dry aprotic solvent such as DMF in the presence of a sterically hindered tertiary amine such as diisopropylethylamine. The product is isolated by diluting with water, adjusting the pH to ~5, washing with an organic solvent, suitably ethyl acetate, and further purifying by recrystallization or chromatography.

When Y is a bond and X is —CON(R$_{18}$)— compounds may also be prepared by reacting equimolar amounts of a 21-iodo steroid derivative of Formula VI and a bis-acid of the formula HOOC—(CH$_2$)$_n$—COOH (Formula VIII) wherein n has the meaning defined in Formula I in a dry aprotic solvent such as THF or DMF in the presence of a sterically hindered amine such as diisopropylethylamine with optional heating to give an intermediate of the formula StOCO(CH$_2$)$_n$—COOH (Formula IX) which is activated by cooling to about −20° to 10° C. and reacting with isobutyl chloroformate in the presence of a tertiary amine, such as triethylamine for about 10–20 minutes during which time the reaction mixture is permitted to warm. To the activated derivative of Formula IX is added an appropriate aminoalkylsulfonate of the formula R$_{18}$NH$_2$—(CH$_2$)$_m$SO$_3$$^-$ (Formula X) wherein m and R$_{18}$ have the meanings defined in Formula I. This latter reaction is complete within an hour, and the product is isolated by standard procedures, e.g., washing an aqueous solution, pH 5, with an appropriate organic solvent such as ethyl acetate, and purification by crystallization and/or chromatography.

Alternatively when Y is a bond and X is —CON(R$_{18}$)— to the above obtained activated derivative of Formula IX is added p-nitrophenol in the presence of a tertiary amine such as triethylamine to give a stable intermediate of the formula StOCO(CH$_2$)$_n$COO—(C$_6$H$_4$)—NO$_2$ (Formula XI) wherein St and n have the meanings defined in Formula I and (C$_6$H$_4$) is 1,4-phenylene. The intermediate of Formula XI is then reacted with a molar equivalent of an aminoalkylsulfonate of Formula X in a dipolar aprotic solvent such as THF or DMF in the presence of a base such as pyridine. The Formula I product is then isolated by washing an aqueous solution at pH 5 with an organic solvent, such as ethyl acetate, and purifying by crystallization and/or chromatography.

The compounds of Formula IV wherein X is —CON(R$_{18}$)— are prepared by heating to about 60° C. a suitable aliphatic lactone, such as propiolactone, γ-butyrolactone, δ-valerolactone, ε-caprolactone, etc., as n in Formula I increases in length, with an equimolar amount of an ω-aminoalkylsulfonate of Formula X in an aprotic solvent such as DMSO, DMF, or THF to give the acyclic amide which is isolated by standard extractive procedures. The amide is reacted with p-nitrophenylchloroformate in a dry aprotic solvent such as THF in the presence of pyridine and isolated by standard procedures to give the compounds of Formula IV or used without isolation to form compounds of Formula I.

The compounds of Formula IV wherein X is —N(R$_{18}$)—CO— are prepared by reacting an appropriate ω-sulfo alkanoic acid having an alkylene chain length of from 1 to 5 carbon atoms with an ω-amino alcohol of the formula HO—(CH$_2$)$_n$—NHR$_{18}$, wherein n and R$_{18}$ have the meanings defined in Formula I, in a dry aprotic solvent, such as THF or DMF, in the presence of dicyclohexylcarbodiimide (DCC) to yield the amide. Any ester formed by reaction at the wrong end of the amino alcohol is eliminated by selective hydrolysis. Alternatively, a cyclic anhydride of Formula A (see Formula Chart) such as 3-sulfopropionic anhydride is reacted with a ω-amino alcohol in a polar aprotic solvent in the presence of a tertiary amine to form the amide. The product is isolated by standard extractive methods, and the product is taken up in a dry aprotic solvent and treated with p-nitrophenyl chloroformate in the presence of pyridine to give the compounds of Formula VIII which may be isolated by standard procedures.

The compounds of Formula IV wherein X is oxygen are prepared by reacting a suitable, α,ω-aliphatic diol of the formula HO(CH$_2$)n—OH wherein n has the meaning defined in Formula I with an ω-halosulfonate of formula Z'—(CH$_2$)$_m$SO$_3$— where Z'=Cl, Br, I, —O—mesyl, or —O—tosyl and m is as defined in Formula I, or, alternatively, with a sultone of Formula B (see Formula Chart) wherein m is as defined in Formula I, in a dry aprotic solvent in the presence of one equivalent of potassium t-butoxide to yield the desired ether. This compound is purified by standard extractive methods, then is reacted with p-nitrophenyl chloroformate in a dry aprotic solvent in the presence of pyridine to give a reactive mixed p-nitrophenyl carbonate ester of Formula IV.

To prepare the compounds of Formula IV wherein X is sulfur, an aliphatic ω-halo alcohol of the formula HO(CH$_2$)$_n$—halo wherein n is as defined in Formula I and halo is chloro, bromo, or iodo is reacted with thiourea in refluxing lower alcohol to yield an isothiouronium salt which is then cleaved by treating the compound with an aqueous base to yield an ω-mercaptoalkanol HS(CH$_2$)$_n$OH—, The ω-mercapto alkanol, after isolation via standard methods, e.g., distillation, is then reacted with an ω-bromoalkylsulfonic acid of formula Br(CH$_2$)$_m$SO$_3$H wherein m is as defined in Formula I or a sultone of Formula B in a solution containing two equivalents of inorganic base in water. A water miscible solvent (e.g., alcohol) may also be added to solubilize the reactants. The product of formula HO(CH$_2$)$_n$S(CH$_2$)$_m$SO$_3$— is isolated by standard extractive procedures. Final purification is achieved by recrystallization and/or chromatography. This product may be oxidized at this stage to give a sulfoxide or sulfone if desired, or it may be maintained in the sulfide form. To form the sulfoxide, i.e., X is —S(O)—, the sulfide is treated with one equivalent of sodium meta periodate in aqueous lower alcohol at 0° C. When oxidation is complete the sodium iodate is filtered out and the sulfoxide isolated by standard procedures. To form the sulfone, i.e., X is —S(O$_2$)—, the sulfide is reacted with 30% H$_2$O$_2$ in 50% acetic acid at room temperature for several hours. Oxidation proceeds through the sulfoxide to the sulfone. The product is isolated by standard procedures, with final purification being achieved by recrystallization or by chromatography if needed. The sulfur-linked hydroxyl containing sulfonate is then converted to a reactive mixed carbonate ester by combining it with an equimolar quantity of p-nitrophenylchloroformate in an aprotic solvent with added pyridine to give the compounds of Formula IV which may be isolated by standard procedures.

The compounds of Formula IV wherein X is a bond are prepared by reacting a sulfoalkanol of the formula HO(CH$_2$)$_{n'}$SO$_3$H (Formula XII) wherein n is from 5 to 10 with p-nitrophenylchloroformate in a dry polar aprotic solvent such as DMF or DMSO in the presence of a tertiary amine such as triethylamine. The reaction product is isolated by standard procedures to give a compound of Formula IV or is used without isolation to prepare compounds of Formula I.

The compounds of Formula XII may be prepared by reacting an alcohol of the formula HO—(CH$_2$)$_{n'}$—R$_b$ wherein n' has the meaning defined in Formula XII and R$_b$ is Cl, Br, I, OS(O$_2$)CH$_3$ or OS(O$_2$)—(C$_6$H$_4$)—CH$_3$ with a sulfite salt such as sodium sulfite in a mixture of water and a water miscible alcohol such as ethanol or propanol. The reaction mixture is heated to reflux and when the desired product formation has taken place, the product may be isolated by standard extractive methods and/ or by crystallization.

Alternatively the compounds of Formula XII may be synthesized in two steps involving the free radical addition of thiolacetic acid to a compound of the formula HO—(CH$_2$)$_{n'-2}$—CH=CH$_2$ wherein n' has the meaning defined in Formula I, followed by oxidation of the resulting thiolacetate with hydrogen peroxide in acetic acid to form compounds of Formula XII. The addition reaction is carried out in the presence of ultraviolet radiation or a peroxide catalyst such as dibenzoyl peroxide. The oxidation is carried out in acetic acid to which 90% hydrogen peroxide has been added and is heated to 65°-70° C. The products are isolated by standard methods.

The compounds of Formula V wherein X is a bond are prepared by reacting a bromoalkanoate of the formula Br—(CH$_2$)$_{n'}$—COO— wherein n' is from 5 to 10 with a molar excess of a sulfite salt in refluxing water or a mixture of water and a water miscible alcohol. The product may be isolated by crystallization or by standard extractive methods. Alternatively the compounds of Formula V wherein X is a bond may be obtained in two steps by first reacting a terminal is from 5 to 10 molar excess of a sulfite salt in refluxing water or a mixture of water and a water miscible alcohol. The product may be isolated by crystallization or by standard extractive methods. Alternatively the compounds of Formula V wherein X is a bond may be obtained in two steps by first reacting a terminal olefin of the formula CH$_2$=CH—(CH$_2$)$_{n'-2}$—COOH wherein n' is from 5 to 10 with thiolacetic acid in the presence of ultraviolet radiation or a peroxide catalyst such as dibenzoyl peroxide under an inert atmosphere (e.g., N$_2$) to form a terminal thiolacetate of the formula CH$_2$—CO—S—(CH$_2$)$_{n'}$—COOH wherein n' is 5 to 10. The thiolacetate is isolated by standard methods and is then oxidized by treatment with hydrogen peroxide in acetic acid. The product of oxidation is a sulfoalkanoic acid of Formula V which may be isolated by standard methods.

The compounds of Formula V wherein X is —N(R$_{14}$)CO— are prepared by reacting an amino acid of the formula HN(R$_{14}$)(CH$_2$)$_n$—COOH with a bromoalkanoyl chloride wherein the alkanoyl moiety contains from 2 to 6 carbon atoms in an aqueous solvent at a pH of about 10 after which the pH is adjusted to about 3. The thus formed amide is extracted with an organic solvent such as ethyl acetate and isolated by procedures generally known in the art then taken up in aqueous alcohol and treated with sodium bisulfite to give the compounds of Formula V which are isolated by standard procedures. Alternatively, the ω-amino acid may be reacted with a cyclic anhydride of Formula A (see Formula Chart) wherein m has the meaning defined in Formula I in an aprotic solvent or in aqueous media in the presence of a tertiary amine to yield the compounds of Formula V.

The compounds of Formula V wherein X is —CON(R$_{14}$)— are prepared by reacting an appropriate alkylene dicarboxylic acid with an appropriate aminoalkylsulfonate by procedures well known in the art.

The compounds of Formula V wherein X is oxygen are prepared using t-butyl ester of a carboxylic acid of the formula t-Bu-OcO(CH$_2$)$_n$—halo wherein n is as defined in Formula I and halo is Cl, Br or I. This ester is prepared by reacting an appropriate ω-halo alkanoic acid of formula HOOC(CH$_2$)$_n$—halo with isobutylene gas in a dry aprotic solvent in the presence of catalytic amounts of sulfuric acid. The butyl ester is reacted with an ω-hydroxyalkyl sulfonic acid of formula HO(CH$_2$)$_m$SO$_3$H wherein m is as defined in Formula I in a dry aprotic solvent in the presence of a strong base such as potassium t-butoxide to yield an ether. The ether is isolated by standard methods well known in the art and the carboxylic acid is deprotected by treatment with trifluoroacetic acid. The compounds of Formula V are isolated by removing trifluoroacetic acid and solvent under reduced pressure.

The compounds of Formula V wherein X is sulfur are prepared by reaction of an ω-mercaptocarboxylic acid of the formula HOOC(CH$_2$)$_n$SH and an ω-bromoalkyl sulfonic acid of formula Br(CH$_2$)$_m$SO$_3$H or a sulfone of Formula B wherein n and m are as defined in Formula I in water containing three equivalents of inorganic base. A water miscible organic solvent, such as THF, may be added if required to solubilize the reactants. After several hours at 30°-50° C. the reaction is complete and the sulfide is isolated by extractive methods to give the compounds of Formula V.

The compounds of Formula V wherein X is sulfoxide are obtained by treating the corresponding Formula P compound wherein X is sulfur with sodium periodate in water at 0° to 10° C. for ~10-20 hours. The aqueous solution is diluted with at least two volumes of acetonitrile, NaIO$_3$ precipitate is filtered out, and the product is isolated by standard methods. The compounds of Formula IV wherein X is sulfone are obtained by treating the corresponding sulfur compound with 30% hydrogen peroxide in 50% acetic acid for several hours at room temperature. The product is again isolated by standard procedures.

The compounds of Formulas VI and VII are prepared by general procedures well known in the art. The bis-acids of Formula VIII and the aminoalkylsulfonates of Formula X are known in the art or are prepared by means well known in the art. Also, the other starting materials described hereinabove including the ω-halosulfonates, the compounds of Formula B, the ω-haloalcohols, the ω-amino acids, the compounds of Formula A, the ω-haloalkanoic acid esters, and the ω-hydroxyalkylsulfonic acids are commercially available, or are known in the art or prepared by procedures generally known in the art.

PREPARATION OF COMPOUNDS OF FORMULA I WHEREIN $R_{11}$ IS $Y'$—$(CH_2)_p$—$X'$—$(CH_2)_q$—$NR_{16}R_{17}$

When $Y'$ is oxy, i.e., —O—, equimolar amounts of an amine of the formula $O_2N(C_6H_4)$—OCO)—$(CH_2)_p$—$X'$—$(CH_2)_q NR_{16}R_{13}$ (Formula XIII) wherein $(C_6H_4)$ is 1,4-phenylene and p, q, $X'$, $R_{16}$ and $R_{17}$, have the meanings defined in Formula I, and a parent steroid of the formula StOH wherein St has the meaning defined in Formula III are reacted in a dry aprotic solvent such as tetrahydrofuran (THF), dimethylformamide (DMF) or dimethylsulfoxide (DMSO), in the presence of an acylation catalyst such as dimethylaminopyridine (DMAP) or N-methylimidazole. Although the reaction may be performed at room temperature it is convenient to gently warm the reaction mixture to about 50°-60° C. with stirring until all the activated carbonate ester is consumed. The product is isolated by pouring the reaction mixture into water with the pH adjusted to 2.4, washing with an organic solvent, e.g., ether or ethyl acetate, then quickly adjusting the pH to 7.8 and extracting with an organic solvent such as ethyl acetate. The product is isolated by removing the solvent and purified by recrystallization or chromatographic techniques.

When $Y'$ is sulfur, i.e., —S—, equimolar quantities of an appropriate thiol amine of the formula $HS(CH_2)_p$—$X'$—$(CH_2)_q$—$NR_{16}R_{17}$ (Formula XIV) wherein p, q, $X'$, $R_{16}$ and $R_{17}$ have the meanings defined in Formula I, and a chloroformate derivative of the parent steroid represented by the formula StOCOCl (Formula XV) wherein St has the meaning defined in Formula III with an equivalent quantity of a tertiary amine, such as triethylamine, are reacted in a dry aprotic solvent such as, THF, DMF or DMSO. The reaction mixture may be warmed gently if desired. The product is isolated by extraction with an organic solvent such as ethyl acetate or hexane and purified by crystallization or chromatography.

When $Y'$ is a bond the compounds are prepared by reacting equimolar amounts of an amino acid of the formula $HOOC(CH_2)_p$—$X'$—$(CH_2)_q$—$NR_{16}R_{17}$ (Formula XVI) wherein p, q, $X'$, $R_{16}$ and $R_{17}$ have the meanings defined in Formula I with a 21-iodo or 21-O-mesyl derivative of the parent steroid which may be represented respectively by the formulas St-Iodo (Formula XVII) and St-O-mesyl (Formula XVIII) wherein St has the meaning defined in Formula III and 21-O-mesyl means —$S(O_2)$—$CH_3$. When the 21-iodo steroid derivative is employed the reaction proceeds at room temperature, whereas when the 21-O-mesyl steroid derivative is used the reaction is heated. Preferably both reactions are heated to about 60°-70° C. The reaction is carried out in a dry aprotic solvent such as DMF in the presence of a sterically hindered tertiary amine such as diisopropylethyl amine. The product is isolated by extraction with an organic solvent, suitably ethyl acetate, and purified by recrystallization or chromatography.

When $Y'$ is a bond and X is —$CON(R_{18})$— the compounds may also be prepared by reacting equimolar amounts of a 21-iodo steroid derivative of Formula XVII and a bis-acid of the formula HOOC—$(CH_2)_p$—COOH (Formula XIX) wherein p has the meaning defined in Formula I in a dry aprotic solvent such as THF or DMF in the presence of a sterically hindered amine such as diisopropylethylamine with optional heating to give an intermediate of the formula St—OOC—$(CH_2)_p$—COOH (Formula XX) which is activated by cooling to about −20° to −10° C. and reacting with isobutyl chloroformate in the presence of a tertiary amine, such as triethyl amine for about 10-20 minutes during which time the reaction mixture is permitted to warm. To the activated derivative of Formula XX is added an appropriate diamine of the formula $R_{18}NH$—$(CH_2)_q NR_{16}R_{17}$ (Formula XXI) wherein q, $R_{16}$, $R_{17}$, and $R_{18}$ have the meanings defined in Formula I. This latter reaction is complete within an hour, and the product is isolated by standard procedures, e.g., extraction with an appropriate organic solvent, such as ethyl acetate and purified by crystallization and/or chromatography.

Alternatively when Y is a bond and X is —$CON(R_{18})$—, to the above obtained activated derivative of Formula XX is added p-nitrophenol in the presence of a tertiary amine such as triethylamine to give a stabile intermediate of the formula $StOOC(CH_2)_p$—$COO(C_6H_4)$—$NO_2$ (Formula XXII) wherein St has the meaning defined in Formula III, and $(C_6H_4)$ is 1,4-phenylene and p has the meaning defined in Formula I. The intermediate of Formula XXII is then reacted with a molar equivalent of an amine of Formula XXI in a dipolar aprotic solvent such as THF or DMF in the presence of a base such as pyridine. The Formula I product is then isolated by extraction with an organic solvent, such as, ethyl acetate and purified by crystallization and/or chromatography.

The compounds of Formula XIII wherein $X'$ is —$CON(R_{18})$— are prepared by heating to about 60° C. a suitable aliphatic lactone, such as, propiolactone, γ-butyrolactone, δ-valerolactone, ε-caprolactone, etc., as q in Formula XXI increases in length, with an equimolar amount of an aliphatic diamine of Formula XXI in an aprotic solvent such as DMSO, DMF or THF to give the acyclic amide which is isolated by diluting the reaction mixture with acidified water, washing with an immiscible solvent, such as ethyl acetate, and adjusting the pH to about 12. The product is extracted with an organic solvent such as ethyl acetate, and the solvent is removed under reduced pressure to give the amide. The amide is reacted with p-nitrophenylchloroformate in a dry aprotic solvent such as THF in the presence of pyridine and isolated by standard procedures to give the compounds of Formula XIII or used without isolation to form compounds of Formula I.

The compounds of Formula XIII wherein $X'$ is —$N(R_{18})$—CO— are prepared by reacting an appropriate N,N dialkyl amino alkanoic acid having an alkylene chain length of from 1 to 5 carbon atoms with a chloroformate ester, such as isobutyl chloroformate, in a dry chilled aprotic solvent, such as THF or DMF, in the presence of a tertiary amine to give the carboxylate-activated amino acid. This solution is then added dropwise with stirring to a second solution containing an equimolar amount of an amino alcohol of the formula HO—$(CH_2)_p$—$NH(R_{18})$ wherein p and $R_{18}$ have the meanings defined in Formula I. An amide is obtained and any ester formed by reaction at the wrong end of the amino alcohol is eliminated by selective hydrolysis. The product is isolated by standard extractive methods, and the oily product is taken up in a dry aprotic solvent and treated with p-nitrophenylchloroformate in the presence of pyridine to give the compounds of Formula XIII which may be isolated by standard procedures.

The compounds of Formula XIII wherein X' is oxygen are prepared by reacting a suitable hydroxyalkoxyalkyl halide of the formula HO—$(CH_2)_p$—O$(CH_2)_q$— halide wherein p and q have the meanings defined in Formula I and halide is, e.g., chloride or bromide with an amine of the formula $HNR_{16}R_{17}$ wherein $R_{16}$ and $R_{17}$ are as defined in Formula I in a dry aprotic solvent with a catalytic amount of NaI present to yield an amino alcohol. After purifying the amino alcohol by extractive methods, it is taken up in a dry aprotic solvent and reacted with p-nitrophenylchloroformate in the presence of pyridine to give a reactive mixed p-nitrophenyl carbonate ester of Formula XIII.

To prepare the compounds of Formula XIII wherein X' is sulfur, an aliphatic ω-halo alcohol of the formula $HO(CH_2)_p$ halo wherein p is as defined in Formula I and halo is chloro or bromo is reacted with an aliphatic thiol of the formula $HS(CH_2)_q NR_{16}R_{17}$ wherein q, $R_{16}$ and $R_{17}$ are as defined in Formula I, to give a sulfide. The reaction is carried out in a partially aqueous solvent with a slight excess of NaOH and a reducing agent, e.g., sodium bisulfite, to inhibit disulfide formation. The product is isolated by extractive methods. This product may be oxidized at this stage to give a sulfoxide or sulfone if desired, or it may be maintained in the sulfide form. To form the sulfoxide, i.e., X' is —S(O)—, the sulfide amino alcohol is treated with one equivalent of sodium metaperiodate in aqueous lower alcohol at 0° C. When oxidation is complete the sodium iodate is filtered out and the sulfoxide isolated by standard procedures. To form the sulfone, i.e., X is —S(O$_2$)—, the sulfide amino alcohol is dissolved in a large excess of 90% formic acid and heated to about 70° C. for several minutes. After cooling to room temperature the solution is treated with 30% hydrogen peroxide. Oxidation proceeds through the sulfoxide to the sulfone. When the oxidation is complete, most of the formic acid is removed under reduced pressure, and the remaining residue is taken up in methanolic HCl. After one hour the mixture is concentrated under reduced pressure to give the desired sulfone-linked amino alcohol as the HCl salt. Final purification is achieved by recrystallization or by chromatography if needed. The sulfur-linked amino alcohol is then converted to a reactive mixed carbonate ester by combining it with an equimolar quantity of p-nitrophenylchloroformate in an aprotic solvent with added pyridine to give the compounds of Formula XIII which may be isolated by standard procedures.

The compounds of Formula XIII wherein X' is a bond are prepared by reacting an amino alkanol of the formula $HO(CH_2)_p$—$NR_{16}R_{17}$ wherein p, $R_{16}$ and $R_{17}$ are as defined in Formula I with p-nitrophenylchloroformate in a dry aprotic solvent, such as, THF in the presence of an amine, such as, triethylamine. The amino alkanol compounds are known in the art or are prepared by generally known procedures by treatment of an appropriate ω-iodoalkanol with an amine of the formula $NHR_{16}R_{17}$ wherein $R_{16}$ and $R_{17}$ are as defined in Formula I.

The compounds of Formula XIV wherein X' is a bond are prepared by reacting equimolar amounts of an ω-haloalkylamine of the formula halo-$(CH_2)_p$—$NR_{16}R_{17}$ wherein halo is halogen and p, $R_{16}$ and $R_{17}$ are as defined in Formula I and thiourea in propylene glycol at an elevated temperature. When the halide has been displaced, the isothiouronium salt is cleaved by adding an amine such as tetraethylene pentamine and continuing to apply heat. When the free thiol has formed, this product is isolated by extractive means or by distillation under reduced pressure.

The compounds of Formula XVI wherein X' is a bond are known in the art or are prepared by procedures well known in the art.

To prepare the compounds of Formula XVI wherein X' is —CON($R_{18}$)— an ω-haloalkyl$C_{2-9}$— carboxylic acid is reacted with equimolar quantities of triethylamine and isobutylchloroformate at −10° C. in an aprotic solvent, preferably THF. The solution is allowed to warm to room temperature and a diamine of the formula $NH(R_{18})(CH_2)_q NR_{16}R_{17}$ wherein $R_{18}$, $R_{16}$, $R_{17}$ and q have the meanings defined in Formula I is added. After about 30 minutes the amide product is isolated by extractive procedures. This product is then reacted with an equimolar amount of thiourea in propylene glycol at an elevated temperature. When the halide has been displaced, the isothiouronium salt is cleaved by adding an amine such as tetraethylene pentamine and continuing to apply heat. When the free thiol has formed, this product is isolated by extractive means or by distillation under reduced pressure.

To prepare compounds of Formula XIV wherein X' is —N($R_{18}$)CO— an amino acid of the formula $HOOC(CH_2)_q NR_{16}R_{17}$ wherein q, $R_{16}$ and $R_{17}$ are as defined in Formula I is activated by reaction with isobutyl chloroformate in a chilled dry aprotic solvent, such as THF, with sufficient triethylamine to take up the liberated HCl. This solution is allowed to warm to room temperature and is then added dropwise under nitrogen to a solution containing an amino alcohol of the formula $HO(CH_2)_p NH (R_{18})$ wherein p and $R_{18}$ are as defined in Formula I. The amide thus obtained is purified by standard procedures. This amide is then dissolved in pyridine and is treated with methane sulfonyl chloride to give the terminal mesyl group. The pyridine is removed under reduced pressure, and the product is heated with a 10% molar excess of thiourea in propylene glycol. When the displacement of the mesyl group by thiourea is complete the resulting isothiouronium salt is cleaved by heating with added tetraethylenepentamine to give the compounds of Formula XIV which are isolated by extractive procedures or by distillation.

The compounds of Formula XIV wherein X' is oxygen are prepared by reacting an N,N-disubstitutedamino alcohol of the formula $HO(CH_2)_q NR_{16}R_{17}$ wherein q, $R_{16}$ and $R_{17}$ are as defined in Formula I with an equimolar quantity of sodium hydride in DMF to form the sodium alkoxide. This solution is then added dropwise to a large molar excess of an aliphatic $C_{2-9}$ dihalide or a dimesylate in DMF. If the halogen groups are chloride, sodium iodide is added as a catalyst. When ether formation is complete, the desired mono ether is isolated by extractive procedures then treated with thiourea in refluxing 95% ethanol to yield the isothiouronium salt. This salt is cleaved by treating the solution with a slight molar excess of sodium hydroxide solution and continuing to reflux the mixture under nitrogen. The amino thiol is then isolated from the reaction mixture by extractive procedures to give the compounds of Formula XIV.

The compounds of Formula XIV wherein X' is sulfur are prepared as follows. An N,N-disubstitutedamino thiol of the formula $HS(CH_2)_q$—$NR_{16}R_{17}$ wherein q, $R_{16}$ and $R_{17}$ are as defined in Formula I is dissolved in a lower alcohol and treated with a slight molar excess of NaOH. This solution is then added, dropwise to a large molar excess of a dibromide of the formula $Br(CH_2)_p Br$ wherein p is an integer from 2 to 9, in an aprotic solvent such as DMF or THF. The desired monosulfide is isolated by standard extractive procedures. At this stage, the sulfide could be oxidized, if desired, to give either the sulfoxide or the sulfone. To prepare the compounds of Formula XIV wherein X' is sulfoxide the sulfide obtained above is treated with sodium metaperiodate in a lower aqueous alcohol by procedures analogous to those described hereinabove in connection with the preparation of compounds of Formula XIII. To prepare the compounds of Formula XIV wherein X' is sulfone the sulfide is dissolved in glacial acetic acid and treated with 30% hydrogen peroxide thus oxidizing the sulfide through the sulfoxide to the sulfone. Whether or not further oxidation is elected, the subsequent steps are the same. The sulfur-linked amino bromide is treated with an equimolar amount of thiourea in refluxing 95% ethanol to yield an isothiouronium salt. This salt is cleaved by the addition of concentrated base to yield the free thiol. Upon acidification and extractive workup the compounds of Formula XIV are obtained.

The steroid chloroformates of Formula XV are prepared by reacting the parent 21 hydroxy steroid with a molar excess of phosgene in THF in a chilled reaction vessel which is then allowed to warm to room temperature. After about one hour the solution is concentrated under reduced pressure and the chloroformate precipitates out.

The compounds of Formula XVI wherein X' is $-N(R_{18})CO-$ are prepared by reacting an aminoacid of the formula $HN(R_{18})(CH_2)_p-COOH$ with a $\omega$-bromoalkanoyl chloride wherein the alkanoyl moiety contains from 2 to 6 carbon atoms in an aqueous solvent at a pH of about 10 after which the pH is adjusted to about 3. The thus formed amide is extracted with an organic solvent such as ethyl acetate and isolated by procedures generally known in the art then taken up in an aprotic solvent such as THF or DMF and treated with an amine of the formula $HNR_{16}R_{17}$ wherein $R_{16}$ and $R_{17}$ have the meanings defined in Formula I to give the compounds of Formula XVI which are isolated by standard procedures.

The compounds of Formula XVI wherein X' is $-CON(R_{18})-$ are prepared by reacting an appropriate alkylene dicarboxylic acid with an appropriate alkylenediamine by procedures well known in the art.

The compounds of Formula XVI wherein X' is oxy are prepared as follows. A t-butyl ester of a carboxylic acid of the formula $t-bu-OCO(CH_2)_{p-1}-CH_2-R_b$ wherein p is as defined in Formula I and $R_b$ is a leaving group such as chloro, bromo, iodo, O-mesyl or O-tosyl is treated with an $\omega$-hydroxy amine of the formula $HO(CH_2)_qNR_{16}R_{17}$ wherein q, $R_{16}$ and $R_{17}$ are as defined in Formula I, e.g., 2-diethylamino ethanol, and an equimolar amount of a strong non-nucleophilic base, e.g., potassium t-butoxide, in a dry aprotic solvent, e.g., THF, to yield the ether coupled promoiety. If the displaceable group is chloro or bromo, NaI may be added as a catalyst. When the ether formation is complete the product is isolated by extractive methods. The t-butyl ester is hydrolyzed by treatment with toluene sulfonic acid in an organic solvent, e.g., toluene, or with anhydrous trifluoroacetic acid to give the compounds of Formula XVI.

The compounds of Formula XVI wherein X' is sulfur are prepared by reaction of an $\omega$-mercaptocarboxylic acid of the formula $HOOC(CH_2)_pSH$ and an $\omega$-halo amino of the formula $halo(CH_2)_qNR_{16}R_{17}$ wherein p, q, $R_{16}$ and $R_{17}$ are as defined in Formula I and halo is chloro or bromo, in aqueous base containing a reducing agent, such as $K_2S_2O_5$. The pH is by addition of base if necessary. A water miscible organic solvent, such as THF, may be added if required to solubilize the $\omega$-haloamine. When the reaction is complete the sulfide is isolated by extractive methods to give the compounds of Formula XVI.

The compounds of Formula XVI wherein X' is sulfur are obtained by treating the corresponding Formula XVI compound wherein X' is sulfur with sodium periodate in a lower aqueous alcohol as described hereinabove. The compounds of Formula XVI wherein X' is sulfone are obtained by treating the corresponding sulfur compound with hydrogen peroxide in 50% acetic acid by procedures analogous to those described hereinbefore.

The compounds of Formulas XVII and XVIII are prepared by general procedures well known in the art. The bis-acids of Formula XIX and the alkylenediamines of Formula XXV are known in the art or are prepared by means well known in the art.

The $\omega$-mercaptocarboxylic acids employed hereinabove are obtained by treating an acid of the formula $HOOC(CH_2)_pR_c$ wherein $R_c$ is chloro, bromo, iodo, O-mesyl or O-tosyl and p is 2 to 9 with thiourea in a refluxing lower alcohol to give the isothiouronium salt which is subsequently cleaved by addition of aqueous base under reducing conditions to give the free thiol group.

The $\omega$-haloamines employed hereinabove wherein m is other than 2 are obtained by adding a secondary amine of the formula $HNR_{16}R_{17}$ wherein $R_{16}$ and $R_{17}$ are as defined in Formula I portionwise to a molar excess of an appropriate $\omega,\omega$-alkylenedihalide. Generally the reaction mixture is heated and if the halide is chloride, an iodide salt may be added as a catalyst. The $\omega$-haloamines wherein q is 2 are commercially available.

PREPARATION OF COMPOUNDS OF FORMULA I WHEREIN $R_{11}$ IS $Z-(CH_2)_rQ$

When Z is a bond, Q is $R_{19}-CH_2COOH$ and $R_{19}$ is $-S-$, $-S(O)-$ or $-S(O)_2-$ the compounds are prepared by reacting a corticosteroid of the formula $St-X_5$ (Formula XXIII) wherein St has the meaning defined in Formula III and $X_5$ is $-OSO_2CH_3$ or iodo, with a molar excess of a compound of the formula $HOOC(CH_2)_r-R_{19}-CH_2COOH$ (Formula XXIV) wherein $R'_{19}$ is $-S-$, $-S(O)-$, or $-S(O)_2-$ and r is an integer from 2 to 9. The reaction is carried out in a polar aprotic solvent such as DMF or DMSO in the presence of at least two moles of an appropriate base per mole of the compound of Formula XXIV. The most preferred base is a bicyclic amidine such as 1,8-diazabicyclo[5.4.0]undec-7-ene (DBU).

Compounds of Formula XXIV wherein $R'_{19}$ is $-SO_2-$ are prepared by treating a compound of the formula $HOCO(CH_2)_rSCH_2-COOH$ (Formula XXV) with a strong oxidant such as 1:1 mixture of glacial acetic acid and 30% hydrogen peroxide. Compounds of Formula XXVII wherein $R_{19}$ is $-SO-$ are prepared by treating a compound of Formula XXV with an equimolar amount of sodium periodate ($NaIO_4$) in aqueous methanol at 0° to 10° C. for approximately one day. The reaction should be monitored to prevent over oxidation to the sulfone. Compounds of Formula XXV are prepared by reacting one equivalent of a compound of the formula $HOCO(CH_2)_rBr$ (Formula XXVI) with one equivalent of mercaptoacetic acid in water in the presence of three equivalents of strong base such as NaOH or KOH.

When Z is a bond, Q is $R_{19}$—$CH_2COOH$ and $R_{19}$ is —$N(R_{20})SO_2$— the compounds are prepared by treating a compound of the formula HOOC—$(CH_2)_r$N$(R_{20})SO_2CH_2COOH$ (Formula XXVI) wherein r and $R_{20}$ are as defined in Formula I with one equivalent of a compound of Formula XXIII wherein $X_5$ is iodo, in a polar aprotic solvent such as dimethyl formamide, dimethyl sulfoxide or tetrahydrofuran in the presence of at least two equivalents of a bicyclic amidine such as 1,8-diazabicyclo[5.4.0]undec-7-ene or a sterically hindered tertiary amine such as diisopropylethylamine. Preferably the reaction is carried out at room temperature using two equivalents of DBU.

Compounds of Formula XXVII are prepared by treating compounds of the formula $R_aOOC(CH_2)_rN(R_{20})SO_2CH_2COOR_a$ (Formula XXVIII) with aqueous mineral acid.

In Formula XXVIII r and $R_{20}$ are as defined in Formula I and $R_a$ is a lower alkyl($C_1$-$C_4$) straight or branched chain. Compounds of Formula XXVIII are prepared by treating an amino acid ester of the formula $R_aOOC(CH_2)_rN(R_{20})H$ wherein $R_a$, r and $R_{20}$ are as defined in Formula XXVIII with a sulfonyl chloride of the formula $ClSO_2CH_2COOR_a$ wherein $R_a$ is as defined in Formula XXVIII in a polar aprotic solvent in the presence of pyridine as a catalyst. The amino ester compounds are prepared by refluxing an amino acid of the formula HOOC$(CH_2)_r$N$(R_{20})$H wherein r and $R_{20}$ are as defined in Formula I in an appropriate lower alcohol in the presence of a catalytic amount of sulfuric acid or anhydrous hydrochloric acid. The amino acids are known in the art or are obtained by treating an acid of the formula HOOC$(CH_2)_r$L wherein L is Cl, Br, I, O-mesyl or O-tosyl with an amine of the formula $R_{20}NH_2$. The sulfonyl chloride compounds are prepared by treating a sulfoacetic acid of the formula $HSO_3CH_2COOR_a$ *wherein Ra is as defined above with thionyl chloride in an aprotic solvent or neat with excess thionyl chloride. Dimethylformamide may be added as a catalyst. The sulfoacetic acids are prepared by esterification of sulfoacetic acid in a refluxing lower alcohol.

When Z is a bond, Q is $R_{19}$—$CH_2COOH$ and $R_{19}$ is —$SO_2N(R_{20})$— the compounds are prepared by condensing a bis-acid of the formula HOOC—$(CH_2)_r$SO$_2$N$(R_{20})$CH$_2$COOH (Formula XXIX) wherein r and $R_{20}$ are as defined in Formula I with a compound of Formula XXVI wherein $X_5$ is iodo in a polar aprotic solvent in the presence of at least two equivalents of DBU or a hindered tertiary amine per equivalent of compound of Formula XXIX. The compounds of Formula XXIX are prepared by acid or base hydrolysis of the corresponding bis ester, i.e., a compound of formula $R_aOOC(CH_2)_rSO_2N(R_{20})CH_2COOR_a$ wherein $R_{20}$, r and $R_a$ are as defined hereinabove, and the bis ester is obtained by condensing an amine ester of the formula H$(R_{20})$NCH$_2$COOR$_a$ with sulfonyl chloride of the formula $R_aOOC(CH_2)_rSO_2Cl$ in a polar aprotic solvent such as dimethyl formamide, tetrahydrofuran or dimethylsulfoxide in the presence of pyridine as a catalyst. The sulfonyl chloride is obtained by treating an acid of the formula HOOC$(CH_2)_r$R$_b$ wherein R$_b$ is, e.g., Cl, Br, I, O-mesyl or O-tosyl with sodium sulfite in aqueous methanol or ethanol at reflux to give the sulfonic acid HOOC$(CH_2)_n$SO$_3$H which is further refluxed in an anhydrous lower alcohol to give the carboxy ester derivative which is treated with excess thionyl chloride in the presence of a catalytic amount of dimethyl formamide.

When Z is —O—, Q is $R_{19}CH_2COOH$ and R $_{is}$ S, S(O) or S(O)$_2$, the compounds are prepared by reacting a steroid StOH wherein St is as defined in Formula III with a compound of the formula $R_cOCOO(CH_2)_r$—R'$_{19}$—CH$_2$COOR$_g$ (Formula XXX) wherein $R_c$ is p-nitrophenyl, R'$_{19}$ is S, S(O) or S(O)$_2$, and r is an integer of from 2 to 9, and $R_g$ is CH$_3$ or 2,2,2-trichloroethyl in a polar aprotic solvent such as tetrahydrofuran, dimethylformamide or 4-dimethylsulfoxide in the presence of an acylation catalyst such as dimethylaminopyridine (DMAP) or N-methyl imidazole and subsequently acid hydrolyzing the resulting ester to the corresponding acid. The Formula XXX compounds are prepared by treating an alcohol of the formula HO(CH$_2$)$_r$—R'$_{19}$—CH$_2$COOR$_g$ wherein R'$_{19}$, r, and $R_g$ are as defined above with equimolar amounts of p-nitrophenyl chlorocarbonate and a tertiary amine, e.g., triethylamine or pyridine in an aprotic solvent such as acetone, chloroform or tetrahydrofuran. The alcohols wherein R'$_{19}$ is —S— are obtained by reacting one equivalent of a compound of the formula HO(CH$_2$)$_r$R$_b$ wherein r is 4 to 9 and R$_b$ is Cl, Br, I, O-mesyl or O-tosyl with one equivalent of mercapto-acetic acid in water in the presence of sodium hydroxide or potassium hydroxide. The thus obtained compounds of the HO(CH$_2$)$_r$—S—CH$_2$COOH are esterified, e.g., by treatment with a catalytic amount of a strong acid such as sulfuric acid or toluene sulfonic acid in methanol at reflux or by treatment with 2,2,2-trichloroethanol in the presence of a catalytic amount of a mineral acid at 65°–95° C. Following esterification the sulfur compounds can be oxidized to the sulfone by treatment with an equimolar amount of NaIO$_4$ in an aqueous alcohol at 0° to 10° C. or to the sulfoxide by treatment with potassium hydrogen persulfate in aqueous alcohol. These oxidation steps may convert the carboxy methyl ester to the free acid and thus the resulting sulfone and sulfoxide can be reesterified as generally described above.

When Z is —O—, Q is —$R_{19}$—$CH_2COOH$, and $R_{19}$ is —$SO_2N(R_{20})$— the compounds are prepared by treating a compound of the formula $R_cOCOO$—$(CH_2)_r$SO$_2$N$(R_{20})$CH$_2$COOCH$_3$ (Formula XXXI) wherein $R_{20}$ and r are as defined in Formula I and $R_c$ is p-nitrophenyl with a corticosteroid of the formula StOH wherein St is as defined in Formula III in a polar aprotic solvent such as dimethylformamide, tetrahydrofuran, or dimethylsulfoxide in the presence of one equivalent of a tertiary amine such as pyridine or triethylamine and a catalytic amount of an acylation catalyst such as 4-dimethylaminopyridine or N-methylimidazole and selectively hydrolyzing the resulting ester to the acid by treating the ester with an aqueous solution of a strong acid such as hydrochloric or sulfuric. The Formula XXXI compounds are prepared by treating a sulfonyl chloride of the formula $R_cOCOO(CH_2)_rSO_2Cl$ wherein r and $R_c$ are as defined above with two equivalents of the methyl ester or the 2,2,2-trichloroethyl ester of glycine or N-alkyl($C_1$-$C_4$) glycine in a suitable aprotic solvent such as tetrahydrofuran, dimethylformamide or dioxane. The sulfonyl chlorides are obtained by reacting an alcohol of the formula HO(CH$_2$)$_r$R$_b$ wherein r and Rb are as defined hereinabove with a sulfite salt such as sodium sulfite in an aqueous lower alkanol at reflux to give compounds of the formula HO(CH$_2$)-

$_r$SO$_3$Na which are reacted with p-nitrophenylchloroformate in a dry polar aprotic solvent such as dimethylformamide or dimethylsulfoxide in the presence of a suitable amount of a tertiary amine such as trialkyl amine or pyridine at 0° to 20° C. to give compounds of the formula R$_c$OCOO(CH$_2$)$_r$—R$_d$ wherein R$_c$ is p-nitrophenyl, r is 4–9, and R$_d$ is a trialkyl(C$_1$–C$_4$) ammonium or pyridinium which are treated with thionyl chloride either using excess thionyl chloride as solvent or using an aprotic solvent such as dimethylformamide.

When Z is —O—, Q is R$_{19}$CH$_2$COOH and R$_{19}$ is —N(R$_{20}$)SO$_2$— the compounds are prepared by treating a steroid of the formula StOH wherein St has the meaning defined in Formula VII with a compound of the formula R$_c$OCOO(CH$_2$)$_r$N(R$_{20}$)SO$_2$CH$_2$COOCH$_3$ (Formula XXXII) wherein r and R$_{20}$ are as defined in Formula I and R$_c$ is p-nitrophenyl in a dry polar solvent such as dimethyl formamide or dimethylsulfoxide in the presence of an acylation catalyst such as DMAP or N-methylimidazole. The reaction will proceed at room temperature but is preferably carried out at about 40°–50° C. The resulting ester is then selectively hydrolyzed with an aqueous acid such as hydrochloric, sulfuric or methanesulfonic. The Formula XXXII compounds are prepared by reacting p-nitrochloroformate with an alcohol ester of the formula HO(CH$_2$)$_r$N(R$_{20}$)SO$_2$CH$_2$COOCH$_3$ in a dry polar aprotic solvent in the presence of a tertiary amine. The alcohol esters are obtained by reacting a sulfonyl chloride of the formula ClSO$_2$CH$_2$COOR$_g$ wherein R$_g$ has the meaning defined hereinabove with an amino alcohol of the formula HO(CH$_2$)$_r$NH(R$_{20}$) in an aprotic solvent and a stoichiometric amount of a tertiary amine. The amino alcohols are commercially available or prepared by reacting a primary amine with a halo alcohol, HO(CH$_2$)halo and the sulfonyl chloride is prepared by well known procedures.

When Z is a bond and Q is CO—COOH the compounds are prepared by treating a steroid of the Formula XXIII wherein X$_5$ is iodo with a slight molar excess of a compound of the formula HOCO(CH$_2$)$_r$COCOOH (Formula XXXIII) in a polar aprotic solvent such as dimethylformamide or dimethylsulfoxide at room temperature in the presence of two molar equivalents of an organic base such as a tertiary amine but more preferably a bicyclic amidine such as DBU. The Formula XXXIII compounds are obtained by treating appropriate diesters of dicarboxylic acids with one equivalent of diethyloxalate in the presence of one equivalent of sodium ethoxide in ethanol, or preferably in an aprotic solvent such as diethylether to give after aqueous workup intermediate triesters of the formula alkylOCO(CH$_{2r-1}$)—C(—COCOalkyl)—HCOOalkyl wherein alkyl has 1 to 4 carbon atoms, which are then treated with 4N HCl at 60°–70° C. for 5 to 10 hours to give the α-ketodicarboxylic acids.

The compounds of Formula I wherein Z is —O— and Q is —CO—COOH are prepared by treating a steroid of the formula StOH wherein St is as defined in Formula III with a small molar excess of a compound of the formula R$_c$OCOO(CH$_2$)$_r$COCOOR$_3$ (Formula XXXIV) wherein r is as defined in Formula I, R$_c$ is p-nitrophenyl, and R$_g$ has the meaning defined hereinabove in a polar aprotic solvent at 40°–50° C. in the presence of one equivalent of organic base such as DMAP or a mixture of DMAP and pyridine and selectively hydrolyzing the resulting ester with aqueous acid. The compounds of Formula XXXIV are prepared by treating compounds of the formula HO(CH$_2$)$_r$COCOOH (Formula XXXV) with two equivalents each of triethylamine and p-nitrophenylchlorocarbonate in a suitable solvent such as tetrahydrofuran at 0° C. for 20 minutes then adding excess methanol or 2,2,2-trichloroethanol and one additional equivalent of triethylamine and allowing the mixture to warm to room temperature. The compounds of Formula XXXV are obtained by treating a lactone of Formula C with aqueous potassium hydroxide and treating the resulting potassium alkanoate salt with iodoacetamide to give compounds of the formula HO(CH$_2$)$_r$COOCH$_2$CONH$_2$ which are treated with a stoichiometric amount of chlorotriphenylmethane in dry pyridine at 100° C. for one hour to give compounds of the formula R$_e$O(CH$_2$)$_r$COOCH$_2$CONH$_2$ wherein r is 2 to 8 and R$_e$ is triphenylmethyl. The triphenylmethyl derivatives are treated with aqueous base to give R$_e$O(CH$_2$)$_r$COOH which compounds are treated with excess thionyl chloride then heated at 150°–200° C. for about two hours in the presence of excess cuprous cyanide to give R$_e$O(CH$_2$)$_r$COCN which compounds are treated with concentrated HCl for several days to give HO(CH$_2$)$_r$COCOOH compounds.

The compounds of Formula I wherein Z is a bond and Q is —CON(R$_{21}$)CH(R$_{22}$)COOH are prepared by activating the carboxylic acid of a compound of the formula St—O—CO—(CH$_2$)$_r$COOH (Formula XXXVI) by treatment with stoichiometric amounts of isobutylchloroformate and triethylamine in a dry aprotic solvent at —10° to 0° C. for 15 to 20 minutes, then adding an appropriate amino acid along with one equivalent of pyridine or triethylamine. Appropriate amino acids for this reaction and the one described below are glycine, sarcosine, alanine, aspartic acid, proline, glutamic acid, serine, threonine, cysteine, methionine, tyrosine, or glycylglycine. The compounds of Formula XXXVI are prepared by treating a compound of Formula XXIII, i.e., StX$_5$, with a stoichiometric amount of a sterically hindered tertiary amine such as diisopropyl ethylamine and a large excess of a dicarboxylic acid of the formula HOOC(CH$_2$)$_r$COOH in a polar aprotic solvent. When X$_5$ in Formula XXIII is iodo the reaction is carried out at room temperature and when X$_5$ is O-mesyl the reaction is carried out at about 45°–60° C.

When Z is —O— and Q is —CON(R$_{21}$)CH(R$_{22}$)COOH the compounds are prepared by treating a steroid StOH wherein St has the meaning defined in Formula III with a compound of the formula R$_c$OCOO(CH$_2$)$_r$—CON(R$_{21}$)CH(R$_{22}$)COOCH$_3$ (Formula XXXVII) wherein r, R$_{21}$ and R$_{22}$ are as defined in Formula I and R$_c$ is p-nitrophenyl, in a polar aprotic solvent such as dimethylformamide or dimethylsulfoxide at 40°–50° C. in the presence of one equivalent of a tertiary amine such as pyridine and a catalytic amount of dimethylaminopyridine or N-methylimidazole and subsequently hydrolyzing the thus formed methyl ester derivative to the corresponding free acid using aqueous acid. The Formula XXXVII compounds are prepared by treating a lactone of Formula C with a methyl ester or a 2,2,2-trichloroethyl ester of an appropriate amino acid as identified above in a polar aprotic solvent in the presence of one equivalent of a non-nucleophilic base at elevated temperature to give compounds of the formula HO(CH$_2$)$_r$CON(R$_{12}$)CH(R$_{22}$)—COOCH$_3$ which are treated with a slight excess of p-nitrophenylchlorocarbonate in a dry aprotic solvent at 0° to 20° C. in the presence of a stoichiometric amount of pyridine or a tertiary amine.

The methyl ester of the compounds described herein can be hydrolyzed to the free acid by heating in aqueous acid by well known procedures. The 2,2,2-trichloroethyl ester of the compounds described hereinabove can be converted to the free acid by treatment with zinc and acetic acid as generally described in J. Am. Chem. Soc. 88, 852 (1966). The salts of the compounds of Formula I, are prepared by treating the acid with a suitable base as generally described hereinabove.

As indicated hereinbefore the various parent steroid starting materials, i.e., StOH and $StX_5$ are known in the art or are prepared by procedures well known in the art.

PREPARATION OF COMPOUNDS OF FORMULA I WHEREIN $R_{23}$ IS —O—C(=O)—$(CH_2)_t$COOH

The compounds are generally prepared by treating one equivalent of 21-hydroxy steroid otherwise corresponding to Formula I with 1.2 equivalents of the anhydride of the appropriate bis acid of the formula $HOOC(CH_2)_t$ (Formula XXXVIII) which acids are known in the art, and 0.05 equivalents of potassium carbonate in a tertiary amine, e.g., pyridine. The reaction is carried out at room temperature with stirring for about 20 hours then the reaction mixture was partitioned between methylene chloride and water. The organic phase is washed with water, dried over sodium sulfate, concentrated and the resulting residue crystallized from an appropriate solvent. To form a salt, e.g., the sodium salt, the crystallized compound is stirred in methanol (ration of 20 ml of methanol to 1 g of steroid) and treated with 0.95 equivalents of sodium bicarbonate which was dissolved in a minimum volume of water. The liquids are concentrated, the residue lyophilized overnight after which the solid is triturated with an appropriate solvent and dried. This general procedure may also be used to prepare compounds of Formula I wherein $R_{is}$ —O—C(=O)—$(CH_2)_t$—COOH.

EXAMPLE 1

6α-Fluoro-5β(and α)-4,5-dihydro-21-benzoyl-17-hydroxy-16β-methyl(-pregna-9(11)-ene)-3,20-dione To 9.0 g (19 mmol) of 6α-fluoro-21-benzoyl-17-hydroxy-16β-methyl(pregna-9(11)-ene)-3,20-dione was added 300 ml of EtOAc and 2.7 g of 10% Pd/C. The reaction mixture was placed in a Parr and hydrogenated under 36 pounds pressure, at room temperature, for 18 hours. The reaction mixture was then filtered through celite and washed well with EtOAc to yield, after removal of solvent, 9.2 g (100%) of a mixture of the α and β isomers. HPLC (40:60 $H_2O$:$CH_3CN$) indicated a 3:5 β:α ratio (see analysis for details).

Chromatographing the crude product using 8:1 $CHCl_3$:EtOAc gave 3.21 g (36%) of the faster moving (Rf=0.8 in 4:1 $CHCl_3$:EtOAc) α isomer and 4.49 g (50%) of the slower moving (Rf=0.65) β isomer, (mp: 130° C.). The α isomer, was recrystallized from acetone:hexane to yield 2.976 g of pure material; (mp: 204.5°–208° C.).

EXAMPLE 2

6α-Fluoro 21-acetyl-5β (and α)-4,5-dihydro-17-hydroxy-16β-methyl(pregna-9(11)-ene)-3,20-dione To 7.25 g of the 6α-fluoro-21-acetyl-17-hydroxy-16β-methyl(pregna-9(11)-ene)-3,20-dione was added 300 ml of EtOAc and 2.3 g of 10% Pd/C. The reaction mixture was hydrogenated on a Parr Shaker Apparatus at 22 pounds pressure for 18 hours at room temperature. The reaction was removed from the Parr, filtered (celite), and evaporated to dryness under vacuum to yield 6.1 g of an α/β mixture of isomers. TLC (4:1 $CHCl_3$:EtOAc) showed two materials Rf=0.5 and 6. Chromatography over silica gel using 10:1 $CHCl_3$:EtOAc on a C type column gave 0.4 g of the faster moving α isomer, 3.7 g of a mixture of isomers, and 1.70 g of pure, slower moving, β isomer. The β isomer was recrystallized from EtOAc to yield 0.7 g of pure β. 4.7 g of recovered mixed isomer fractions were rechromatographed to eventually yield 1.33 g of the α isomer (18%), 1.56 g of the β isomer (21%) and 2.9 g (40%) of mixed α/β products (m.p. 188°–194.3° C.).

EXAMPLE 3

6α-Fluoro-5-(α and β)-4,5-dihydro-17-hydroxy-16β-methyl(pregna-9-(11)-ene)-3,20-dione To 300 mg of 6α-fluoro-17-hydroxy-16β-methyl-(pregna-9(11)-ene)-3,20-dione was added 30 ml of EtOAc and 100 mg of 10% Pd/C. The reaction mixture was hydrogenated on a Parr Shaker at 13 pounds pressure at room temperature for 18 hours. The reaction was removed from the Parr, filtered (celite) and washed well with EtOAc. TLC (2:1 $CHCl_3$:EtOAc) indicated two materials, Rf=0.5 and 0.6. HPLC indicated two compounds in approximately 1:1 ratio. The solution was evaporated to dryness to give an amorphous foam. Addition of $CHCl_3$ to the foam resulted in crystallization of the faster moving α isomer; 33 mg (11%); the mother liquors were chromatographed over silica gel using 4:1 $CHCl_3$:EtOAc to yield 62 mg (21%) of the slower moving β isomer. The rest of the material was collected as mixed fractions (145 mg=48%) of α and β isomers.

EXAMPLE 4

6α-Fluoro-21-acetyl-5α-4,5-dihydro-3(α),17-dihydroxy-16β-methyl(pregna-9(11)-ene)-20-one To 0.4 g (0.952 mM) of the 5α isomer product from Example 2 was added 15 ml of dioxane and 2.0 g of washed RaNi. The reaction mixture was placed on a Parr and reduced at 40 pounds pressure at room temperature for 18 hours. TLC (4:1 $CHCl_3$:EtOAc) indicated three materials, Rf=0.75, 0.3, 0.25. TLC 1:2 acetone:cyclohexane also indicated three materials, Rf=0.5, 0.45, 0.4, with the spot at 0.75 in $CHCl_3$:EtOAc=0.4 in acetone:cyclohexane. Filtration and evaporation to dryness gave 360 mg of crude products corresponding to a mixture of the title compounds. Chromatography over silica gel using 1:4 acetone cyclohexane gave 110 mg (27%) of pure title compound, Rf=0.45 in 1:2 acetone:cyclohexane, along with 43 mg (10%) of 90% pure title compound.

EXAMPLE 5

6α-Fluoro-5α-3(α and β)-hydroxy-4,5-dihydro-21-benzoyl-17-hydroxy-16β-methyl(pregna-9(11)-ene)-20-one 2.50 g (5.18 mM) of 6α-fluoro-5α-4,5-dihydro-21-benzoyl-17-hydroxy-16β-methylpregna-9(11)ene-3,20-dione from Example 1 was divided into two portions of 1.25 g each. To each portion was added 5 ml of dioxane and 8.0 g of freshly washed RaNi (washed first with water 3X, then absolute ETOH 3X, followed by dry dioxane 3X). The mixture was placed on a Parr and hydrogenated at 42 pounds pressure at room temperature for 18 hours. The reaction mixture was removed from the Parr, filtered over celite and washed well with dioxane. Evaporation to dryness gave 2.38 g (95% crude) (total from the two reactions) of title compounds.

EXAMPLE 6

6α-Fluoro-5β-4,5-dihydro-21-benzoyl-3(α and β)-17-dihydroxy-16β-methyl(pregna-9(11)-ene)-20-one To 500 mg of 6α-fluoro-5β-4,5-dihydro-21-benzoate-17-hydroxy-16β-methyl(pregna-9(11)ene)-3,20-dione (1.04 mM) from Example 1 was added 15 ml of dioxane and 2.0 g of freshly washed RaNi (washed as described previously). The reaction mixture was placed on a Parr Shaker and reduced under 37 pounds pressure at room temperature for 18 hours. Added an additional 1.0 g of washed RaNi and continued to reduce for an additional 18 hours. At this point the reaction appeared complete by TLC (two spots, Rf=0.4 and 0.5 in 35% EtOAc/Hexane, with starting compound at Rf=0.75). The reaction mixture was filtered, washed well with dioxane, and evaporated to dryness. Chromatography using 5:1 Hexane:EtOAc gave 191 mg (38%) of the faster isomer and 135 mg (27%) of the slower moving 3α isomer. Total recovered yield was 326 mg (65%).

EXAMPLE 7

6α-Fluoro-21-acetyl-5β-4,5-dihydro-3(β and α), 17-dihydroxy-16β-methyl(pregna-9(11)-ene)-20-one and
6α-Fluoro-17-acetyl-5β-4,5-dihydro-3(β),21-dihydroxy-16β-methyl(pregna-9(11)-ene)-20-one To 0.50 g (1.19 mM) of the 5β-isomer product from Example 2 was added 15 ml of dioxane and 2.0 g of washed RaNi (washed as previously described). The reaction mixture was placed in a Parr Shaker and reduced at 40 pounds pressure for 18 hours. The reaction appeared complete and was removed from the Parr, filtered (celite), and evaporated to dryness to yield 0.60 g of crude title compounds. Chromatography over silica gel using 4:1 CHCl$_3$:EtOAc gave two fractions. The faster moving fractions 0.160 g (Rf=0.6; 2:1 CHCl$_3$:EtOAc) contained two materials after chromatography (by TLC, Rf=0.25 and 0.28; 1:2 acetone:cyclohexane and by HPLC, 50:50 H$_2$O:CH$_3$CN; 2.65 and 3.91 minutes; ratio 1:2) while the slower moving product 0.130 g was a single material under the same conditions (Rf=0.4; 2:1 CHCl$_3$:EtOAc) and was determined to be the 3α isomer. The faster moving material was rechromatographed using 7.1 CHCl$_3$:EtOAc to give 57 mg of the faster moving 3β-21-acetate, and 84 mg of the 3β-17-acetate.

EXAMPLE 8

6α-Fluoro-5β-4,5-dihydro-3α,17-dihydroxy-16β-methyl(pregna-9(11)-ene)-20-one

To 204 mg (0.539 mM) of the 5β-isomer product of Example 3 was added 25 ml of isopropanol. The mixture was warmed until all the solids dissolved. The solution was then cooled to room temperature and 10 mg of NaBH was added. The reaction was stirred at ambient temperature for 3 hours. Three ml of H$_2$O was added and the reaction was evaporated to dryness under vacuum. The residue was separated between H$_2$O and EtOAc and the organic layer washed well with water. The EtOAc was dried over Na$_2$SO. filtered, and evaporated to dryness under vacuum. TLC (10% isopropanol/CHCl$_3$) indicated three materials Rf=0.3, 0.4, and 0.6. Chromatography over silica gel using 10% isopropanol/CHCl$_3$ gave 88 mg (43%) of the title compound, Rf=0.6 in 10% isopropanol/CHCl$_3$ as described above.

EXAMPLE 9

6α-Fluoro-5β-4,5-dihydro-3α,17-dihydroxy-16β-methyl(pregna-9(11)diene)-20-one

To 120 mg (0.25 mM) of 6α-fluoro-5β-4,5-dihydro-21-benzoyl-3α,17-dihydroxy-16β-methyl(pregna-9(11))-ene)-20-one (product of Example 5) was added 5.0 ml of methanol and five drops of a 25% CH$_3$ONa/CH$_3$OH solution. The reaction mixture was allowed to sit at room temperature for one hour. At this time all the starting material had disappeared (by TLC 35% EtOAc/Hexane) and CO$_2$ chips were added to the resulting solution to neutralize. Evaporating the solution to dryness gave crude title compound (R$_f$ 0.35 in 1:1 cyclohexane:acetone, m.p. 174°–179° C.).

EXAMPLE 10

6α-Fluoro-5β-4,5-dihydro-3(β and α),17-dihydroxy-16β-methyl(pregna-9(11)diene)-20-one To 365 mg (0.869 mM) of the crude acetate product mixture (3β and 3α) prepared as in Example 7 was added 10 ml of CH$_3$OH and 10 drops of a 25% CH$_3$ONa/CH$_3$OH solution. After sitting at room temperature for 2½ hours an additional 1.5 ml of 25% CH$_3$ONa/CH$_3$OH was added. After 8 minutes the reaction appeared complete. The solution was neutralized by the addition of CH$_3$COOH, evaporated to dryness under vacuum, and dissolved in CHCl$_3$. Darco was added to the CHCl$_3$ solution, the mixture filtered and the pad washed well with CHCl$_3$. Evaporation to dryness gave 0.720 g of crude title compound. The crude residue was dissolved in acetone (10 ml), filtered from insoluble salts and the solution evaporated to dryness to yield 300 mg. Chromatography over silica gel using 8:1 cyclohexane:acetone gave 22 mg (6.6%) of the faster moving 3β isomer (Rf 0.40 in 1:1 cyclohexane:acetone, m.p. 225°–227° C.) and 28 mg (8.5%) of the slower moving 3α isomer (Rf 0.35 in 1:1 cyclohexane:acetone, m.p. 174°–179° C.).

EXAMPLE 11

6α-Fluoro-5β-4,5-dihydro-3(β and α),17-dihydroxy-16β-methyl(pregna-9(11)diene)-20-one To 0.507 mg (1.20 mM) of a crude mixture of the 3β and 3α products prepared as in Example 4 was added 10 ml of methanol and 10 drops of a 25% solution of $CH_3ONa/CH_3OH$. The solution was allowed to stir at ambient temperature for a period of one hour at which time a few pieces of solid $CO_2$ was added to neutralize. The reaction was evaporated to dryness and the residue dissolved in $CHCl_3$, filtered through celite, and evaporated to dryness under vacuum to yield 530 mg of crude title compound. Chromatography on silica gel using 6:1 cyclohexane:acetone gave 165 mg (36%) of the faster moving 3α isomer (m.p. 212.5°-217° C., Rf 0.5 in 1:1 cyclohexane:acetone and 110 mg (24%) of the slower moving 3β isomer (m.p. 230°-231° C., Rf 0.45 in 1:1 cyclohexane:acetone). Both of the samples could be recrystallized from acetone:hexane to yield analytically pure samples.

EXAMPLE 12

6α-Fluoro-5β-4,5-dihydro-3β,17-dihydroxy-16(pregna-9(11)-ene)-20-one

To 170 mg (0.35 mM) of 6α-fluoro-5β-4,5-dihydro-21-benzoyl-3β,17-dihydroxy-16(pregna-9(11)-ene)-2-one (product of Example 6) was added 5.0 ml of $CH_3OH$ and five drops of 25% $CH_3ONa/CH_3OH$. The reaction appeared complete by TLC (TLC: 35% EtOAc/Hexane; Rf=0.2) after about one hour. $CO_2$ chips were added to neutralize, and the entire reaction mixture was evaporated to dryness under vacuum. The resulting residue was chromatographed using 1:1 EtOAc:Hexane, taking 30 ml fractions silica gel to give 62 mg (49%) of the title product (m.p. 225°-227° C., Rf 0.4 in 1:1 cyclohexane:acetone).

EXAMPLE 13

21-Phosphate-6α-fluoro-17-hydroxy-16β-methyl(pregna-4,9(11)-diene)-3,20-dione

To 1.65 g of 6α-fluoro-17,21-dihydroxy-16β-methyl(-pregna-4,9(11)-diene)-3,20-dione was added 20 ml of tetrahydrofuran (THF) followed by cooling to −35° C. and addition dropwise of a solution of 0.68 ml of distilled pyrophosphoryl chloride in 10 ml of THF. The reaction mixture was stirred at −30° to −35° C. for 2½ hours, treated with 20 ml of $H_2O$, then stirred at ambient temperature for an additional two hours. Added 4.0 g of NaCl, separated the layers, and washed the upper organic layer with saturated NaCl solution. The organic layer was evaporated to dryness and 25 ml of $H_2O$ was added to the resulting residue. Crystallization occurred immediately. The solids were dried at 50° C. to yield 1.82 g (91.5%) of title compound. TLC (70:20:10; isopropanol-$H_2O$-concentrated $NH_4OH$; rf=0.4 with trace quantities of unreacted starting material (by TLC, 4:1 $CHCl_3$:EtOAc)).

Mass Spec. (FAB) M+calculated: 457.1791. Found: 457.1798.

EXAMPLE 14

21-Phosphate-6α-fluoro-17-hydroxy-16β-methyl(pregna-4,9(11)-diene)-3,20-dione disodium salt (prepared from methanol)

To 546 mg of 21-phosphate-6α-fluoro-17-hydroxy-16β-methyl(pregna-4,9(11)-diene)-3,20-dione was added 15 ml of methanol and, when dissolution was complete, a solution of $NaOH/CH_3OH$ (prepared by evaporation of 1.95 ml of a 1N aqueous NaOH solution to dryness, azeotroping the residue with $CH_3OH$, drying under high vacuum at 40° C., and dissolving in 10 ml of $CH_3OH$). After one hour stirring at room temperature 200 mg of activated charcoal was added, the mixture filtered (celite) and the resulting clear solution evaporated to dryness under high vacuum. The residue was triturated with EtOAc followed by acetone to yield, after drying at 40° C., 420 mg (84%) of highly hygroscopic title compound.

Mass Spec. (FAB) calculated: 501.1430. Found: 501.1481.

Example 3 provides an alternative method for the preparation of this compound. The aforedescribed method of Example 2 is preferred, however.

EXAMPLE 15

21-Phosphate-6α-fluoro-17-hydroxy-16β-methyl(pregna-4,9(11)-diene)-3,20-dione disodium salt (prepared from $H_2O$)

To 460 mg of 21-phosphate-6α-fluoro-17-hydroxy-16β-methyl(pregna-4,9(11)-diene)-3,20-dione was added 20 ml of $H_2$) and dropwise, 1.90 ml of a 1N aqueous NaOH solution. When the addition was complete the solution was allowed to stir at room temperature for two hours. The solution was extracted with methylene chloride and the aqueous layer filtered through celite. The resulting clear aqueous solution was lyophilized to yield 550 mg of title compound as a highly hygroscopic solid.

Mass Spec. calculated: 501.1430. Found: 501.1472.

EXAMPLE 16

21-Phosphate-6α-fluoro-17-hydroxy-16β-methyl(pregna-4,9(11)-diene)-3,20-dione

| | |
|---|---|
| disodium salt (prepared from methanol) | 155 mg |
| Dilute NaOH to adjust pH to 5.3 | |
| Sterile water for injection to make 1 mlr | |

EXAMPLE 17

21-Phosphate-6α-fluoro-17-hydroxy-16β-methyl(pregna-4,9(11)-diene)-3,20-dione

| | |
|---|---|
| disodium salt (prepared from methanol) | 153 mg |
| Adipic acid | 7.3 mg |
| Methyl paraben | 1.5 mg |
| Propyl paraben | 0.2 mg |
| NaOH (dilute) to adjust pH to 5.4 | |
| Sterile water for injection make 1 ml | |

EXAMPLE 18

21-Phosphate-6α-fluoro-17-hydroxy-16β-methyl(pregna-4,9(11)-diene)-3,20-dione

| | |
|---|---|
| disodium salt (prepared from methanol) | 166 mg |
| Creatine | 8.0 mg |
| Acetic acid | 4.6 mg |
| Sodium acetate | 2.0 mg |
| Sodium bisulfite | 1.0 mg |
| Disodium edetate | 0.5 mg |
| Benzyl alcohol | 8.8 mg |
| HCl (dilute or NaOH (dilute) to adjust pH to 5.0 | |
| Water for injection to make 1 ml | |

FORMULA CHART

Formula I

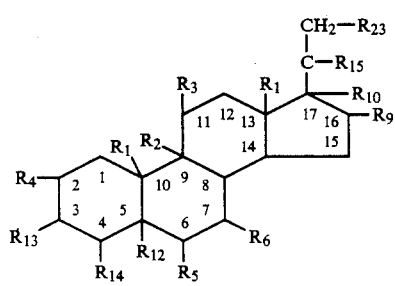

Formula II

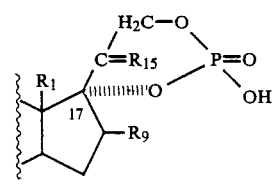

Formula III

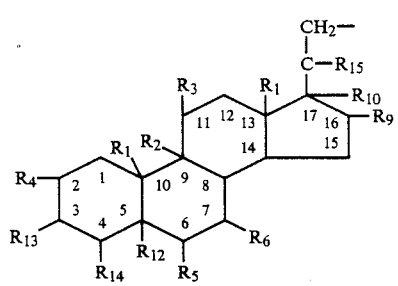

Formula A

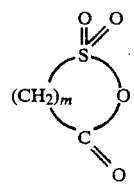

Formula B

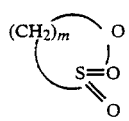

Formula C

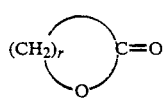

We claim:

1. A compound of the formula

[steroid structure diagram with substituents $R_1$, $R_4$, $R_5$, $R_6$, $R_9$, $R_{10}$, $R_{13}$, $R_{15}$, $R_{23}$]

where $R_1$ is β-CH$_3$ or β-CH$_2$—CH$_3$;

$R_4$ is α-$R_{4-1}$:β-$R_{4-2}$ where one of $R_{4-1}$ and $R_{4-2}$ is —H and the other is —H, —F, —Cl or —CH$_3$;

$R_5$ is α-$R_{5-1}$:β-$R_{5-2}$ where one of $R_{5-1}$ and $R_{5-2}$ is —H and the other is —H, —F, —CH$_3$;

$R_6$ is α-$R_{6-1}$:β-$R_{6-2}$ where one of $R_{6-1}$ and $R_{6-2}$ is —H and the other is —H or —CH$_3$;

(D-I) $R_9$ is =CH$_2$ or α-$R_{9-1}$:β$R_{9-2}$ where one of $R_{9-1}$ and $R_{9-2}$ is —H and the other is —H, or —CH$_3$;

$R_{10}$ is —H, —OH or —CH$_3$;

(D-11) $R_9$ is $R_{9-3}$:$R_{9-4}$ where one of $R_{9-3}$ and $R_{9-4}$ is —H and the other is taken together with $R_{10}$ to form a second bond between the atoms to which $R_9$ and $R_{10}$ are attached;

$R_{13}$ is =O or α-$R_{13-1}$:β-$R_{13-2}$ where one of $R_{13-1}$ and $R_{13-2}$ is —H and the other is —OH, —O—P(O)(OH)$_2$ or —O—CO—(CH$_2$)$_t$—COOH where t is 2 thru 6;

$R_{15}$ is =O or —H:—OH;

$R_{23}$ is (1) taken with $R_{10}$ and the intervening —C—CR$_{15}$—CH$_2$— to form a cyclic phosphate of the formula

[cyclic phosphate structure diagram]

where $R_9$ and $R_{15}$ are as defined above, (2) —OH, (3) —O—CO—$R_{11}$, where $R_{11}$ is (a) —Y—(CH$_2$)$_n$—X—(CH$_2$)$_m$—S$_3$CH, where Y is a bond or —O—, X is a bond, —CON($R_{18}$)— where $R_{18}$ is —H or alkyl(C$_1$-C$_4$), —N($R_{18}$)CO— where $R_{18}$ is as defined above, —O—, —S—, —SO— or —SO$_2$—, n is 4 thru 9 and m is 1 thru 5, (b) —Y'—(CH$_2$)$_p$—X—(CH$_2$)$_q$—NR$_{16}$R$_{17}$, where Y' is a bond, —O— or X is as defined above, p is 2 thru 9, q is 1 thru 5, $R_{16}$ and $R_{17}$ are the same or different and is an alkyl group of from 1 thru 4 carbon atoms optional substituted with 1 —OH or $R_{16}$ and $R_{17}$ can be taken together with the nitrogen atom to which each is attached to form a monocyclic heterocyclic selected from the group consisting of pyrrolidino, piperidino, morpholino, thiomorpholino, piperazino or N(lower)alkylpiperazino wherein lower alkyl is from 1 thru 4 carbon atoms, (c) —Z—(CH$_2$)$_r$Q, where r is 2 thru 9, Z is a bond or —O— and Q is —R$_{19}$—CH$_2$COOH where R$_{19}$ is —S—, —SO—, —SO$_2$—, —SO$_2$N(R$_{20}$)—, where R$_{20}$ is —H or lower alkyl(C$_1$–C$_4$), or —N(R$_{20}$)SO$_2$— where R$_{20}$ is as defined above, with the proviso that the total number of carbon atoms in R$_{20}$ and (CH$_2$)$_r$ is not greater than 10, —CO—COOH or —CON(R$_{21}$)CH(R$_{22}$)COOH where (i) R$_{21}$ is —H and R$_{22}$ is —H, —CH$_3$, —CH$_2$COOH, —CH$_2$CH$_2$COOH, —CH$_2$OH, —CH$_2$SH, —CH$_2$CH$_2$SCH$_3$ or —CH$_2$Ph—OH- where Ph—Oh is p-hydroxyphenyl, (ii) R$_{21}$ is —CH$_3$ and R$_{22}$ is —H, (iii) R$_{21}$ and R$_{22}$ taken together are —CH$_2$CH$_2$CH$_2$—, —NHCH$_2$CONHCH$_2$COOH or —N(R$_{21}$)CH(R$_{22}$)COOH where R$_{21}$ and R$_{22}$ are as defined above, (4) —O—P(O)(OH)$_2$ or (5) —O—CO—(CH$_2$)$_y$COOH where y is 2 thru 6; with the provisos that (a) the sum of m and n is not greater than 10;

(b) the sum of p and q is not greater than 10;

(c) when X is a bond the sum of m and n is from 5 to 10;

(d) when X is a bond the sum of p and q is from 4 to 9;

(e) when R$_9$ is =CH$_2$, R$_{10}$ is other than a second bond between positions C-16 and C17;

(f) R$_{13}$ is —O only when R$_{23}$ with R$_{10}$ and the intervening C—CR$_{15}$—CH$_2$ forms a cyclic phosphate;

and mono and bis salts thereof when R$_{23}$ contains a phosphate, carboxylic acid or sulfate.

2. A compound according to claim 1 where

R$_1$ is β-CH$_3$;

R$_4$ is —H:—H;

R$_5$ is α-R$_{5-1}$:β-R$_{5-2}$ where one of R$_{5-1}$ and R$_{5-2}$ is —H and the other is —H, —F or —CH$_3$;

R$_6$ is —H:—H;

R$_9$ is α-R$_{9-1}$:β-R$_{9-2}$ where one of R$_{9-1}$ and R$_{9-2}$ is —H and the other is —H or —CH$_3$;

R$_{13}$ is α-R$_{13-1}$:β-R$_{13-2}$ where one of R$_{13-1}$ and R$_{13-2}$ is —H and the other is —OH;

R$_{15}$ is =O;

R$_{23}$ is —OH or —O—P(O)(OH)$_2$ and

∼ indicates the attached group can be in either the α or β configuration; and mono and bis salts thereof when R$_{23}$ is a phosphate.

3. A compound according to claim 1 where R$_{9-1}$ is —CH$_3$.

4. A compound according to claim 1 where R$_{9-2}$ is —CH$_3$.

5. A compound according to claim 1 which is selected from the group consisting of 6α-fluoro-3α,17α,21-trihydroxy-16β-methyl-5β-pregn-9(11)-en-20-one, 6α-fluoro-3α,17α,21-trihydroxy-16β-methyl-5α-pregn-9(11)-en-20-one, 6α-fluoro-3α,17α,21-trihydroxy-16β-methyl-5α-pregn-9(11)-en-20-one and 6α-fluoro-3α,17α,21-trihydroxy-16β-methyl-5β-pregn-9(11)-en-20-one.

6. 6α-Fluoro-17α,21-dihydroxy-16β-methylpregna-4,9(11)-diene-3,20-dione 21-phosphate and salts thereof.

7. A compound according to claim 6 which is 6α-fluoro-17α,21-dihydroxy-16β-methylpregna-4,9(11)-diene-3,20-dione 21-phosphate disodium salt.

* * * * *

UNITED STATES PATENT AND TRADEMARK OFFICE
CERTIFICATE OF CORRECTION

PATENT NO. : 4,975,537

DATED : December 4, 1990

INVENTOR(S) : Paul A. Aristoff, et al

It is certified that error appears in the above-identified patent and that said Letters Patent is hereby corrected as shown below:

On the title page before item [57] insert --Attorney, Agent, or Firm - Bruce Stein--.

Signed and Sealed this

Seventh Day of April, 1992

Attest:

HARRY F. MANBECK, JR.

Attesting Officer

Commissioner of Patents and Trademarks